(12) United States Patent
Mizera et al.

(10) Patent No.: US 12,268,623 B2
(45) Date of Patent: Apr. 8, 2025

(54) DEVICE FOR SUPPORTING BOTH ARMS OF A USER

(71) Applicant: OTTOBOCK SE & CO. KGAA, Duderstadt (DE)

(72) Inventors: Oliver Mizera, Göttingen (DE); Annedore Kurzweg, Göttingen (DE); Lüder Mosler, Duderstadt (DE); Samantha Fox, Waitsfield, VT (US); Benjamin Schirrmeister, Göttingen (DE); Matthias Vollbrecht, Herzberg (DE); Meike Kehnen, Göttingen (DE); Sonja Wagner, Vienna (AT)

(73) Assignee: Ottobock SE & Co. KGAA, Duderstadt (DE)

( * ) Notice: Subject to any disclaimer, the term of this patent is extended or adjusted under 35 U.S.C. 154(b) by 1381 days.

(21) Appl. No.: 16/495,004

(22) PCT Filed: Sep. 21, 2017

(86) PCT No.: PCT/EP2017/073947
§ 371 (c)(1),
(2) Date: Nov. 11, 2019

(87) PCT Pub. No.: WO2018/224175
PCT Pub. Date: Dec. 13, 2018

(65) Prior Publication Data
US 2022/0378596 A1    Dec. 1, 2022

(30) Foreign Application Priority Data

Jun. 6, 2017    (DE) .................... 10 2017 112 436.5

(51) Int. Cl.
*A61F 5/00*    (2006.01)
*A61F 5/01*    (2006.01)
(Continued)

(52) U.S. Cl.
CPC ............ *A61F 5/0118* (2013.01); *A61F 5/013* (2013.01); *A61H 1/0274* (2013.01);
(Continued)

(58) Field of Classification Search
CPC ...... A61F 5/0118; A61F 5/013; A61F 5/0102; A61F 2005/0155; A61H 1/0274; A61H 1/0281; B25J 9/0006; B25J 9/108
See application file for complete search history.

(56) References Cited

U.S. PATENT DOCUMENTS 5,405,313 A * 4/1995 Albin .................... A61F 5/026
                                                                    602/5
9,427,865 B2    8/2016 Doyle
(Continued)

FOREIGN PATENT DOCUMENTS

CN    106456339 A    2/2017
CN    102579178 A    7/2017
(Continued)

OTHER PUBLICATIONS

Chinese office action dated May 13, 2022.

*Primary Examiner* — Margaret M Luarca
*Assistant Examiner* — Sarah B Lederer
(74) *Attorney, Agent, or Firm* — WCF IP

(57) ABSTRACT

The invention relates a device for supporting two arms 4 of a user 2 wherein the device has
  two arm support elements 6, each of which has an arm shell 10 for placing on an arm 4,
  at least one passive actuator 26,
    which is configured to apply a force to at least one of the arm support elements 6, and
  at least one counter bearing 14 for the force to be applied, which comprises
    at least one counter bearing element 16 and
(Continued)

Figure 1:
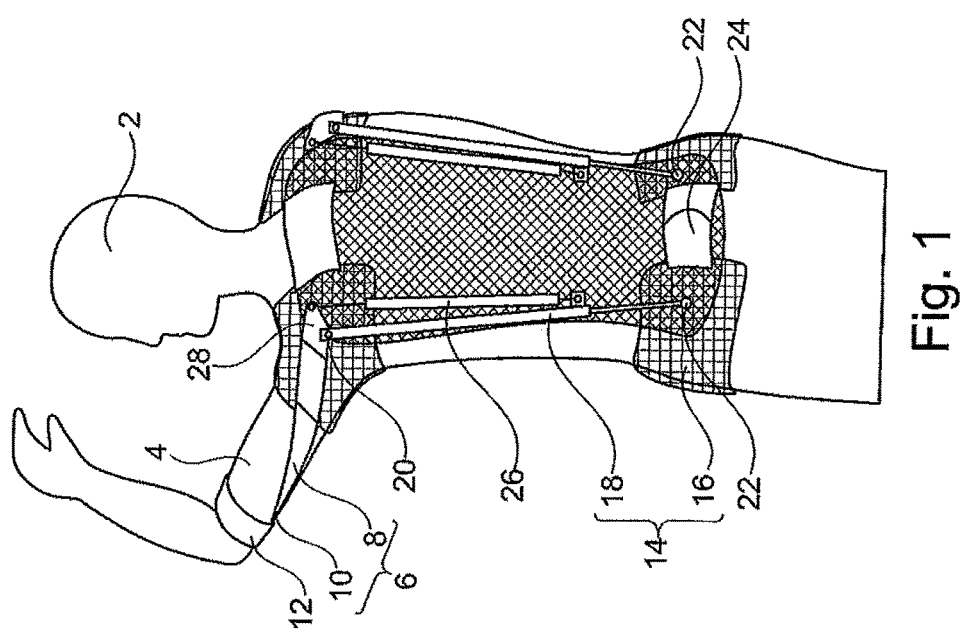

at least two force transmission elements 18, which are configured to transfer a counter force from each of the arm support elements to the counter bearing element 16, wherein the force transmission elements 18 are arranged on the counter bearing element 16 such that they can be moved relative to the counter bearing element 16, in particular they can be rotated about at least one rotational axis.

23 Claims, 21 Drawing Sheets

(51) Int. Cl.
    *A61H 1/02*     (2006.01)
    *A61H 3/00*     (2006.01)
    *B25J 9/00*     (2006.01)
    *B25J 9/10*     (2006.01)

(52) U.S. Cl.
    CPC ............ *A61H 1/0281* (2013.01); *A61H 3/00* (2013.01); *B25J 9/0006* (2013.01); *B25J 9/0009* (2013.01); *B25J 9/108* (2013.01); *A61F 2005/0134* (2013.01); *A61F 2005/0155* (2013.01); *A61F 2005/0179* (2013.01); *A61H 2001/0203* (2013.01); *A61H 2003/007* (2013.01); *A61H 2201/1638* (2013.01); *A61H 2201/165* (2013.01); *A61H 2201/1673* (2013.01); *A61H 2201/168* (2013.01)

(56) References Cited

U.S. PATENT DOCUMENTS

| | | |
|---|---|---|
| 2011/0127390 A1 | 6/2011 | Brown |
| 2011/0164949 A1 | 7/2011 | Kim et al. |
| 2012/0184880 A1 | 7/2012 | Doyle |
| 2014/0033391 A1 * | 2/2014 | Doyle .................... A61B 90/53 2/16 |
| 2014/0378882 A1 | 12/2014 | Kazerooni et al. |
| 2015/0306762 A1 | 10/2015 | Doyle |
| 2016/0081871 A1 | 3/2016 | Doyle |
| 2016/0339583 A1 * | 11/2016 | Van Engelhoven ... B25J 9/0006 |
| 2017/0055883 A1 | 3/2017 | Lee et al. |
| 2018/0360637 A1 | 12/2018 | Doyle |
| 2020/0000611 A1 | 1/2020 | Clausen et al. |

FOREIGN PATENT DOCUMENTS

| | | |
|---|---|---|
| EP | 3 156 193 A1 | 4/2017 |
| JP | 2001-218780 A | 8/2001 |
| JP | 2007-029113 A | 2/2007 |
| JP | 2008-295696 A | 12/2008 |
| JP | 2009-106270 A | 5/2009 |
| JP | 2011188896 A | 9/2011 |
| JP | 2012-239818 A | 12/2012 |
| JP | 2014-172129 A | 9/2014 |
| JP | 2014-239674 A | 12/2014 |
| JP | 2015524752 A | 8/2015 |
| JP | 2017-024086 A | 2/2017 |
| JP | 7107861 B2 | 7/2022 |
| RU | 2005123455 A | 1/2007 |
| RU | 155011 U1 | 9/2015 |
| WO | 2014/093408 A2 | 6/2014 |
| WO | 2014/195373 A1 | 12/2014 |
| WO | WO-2018073629 A1 * | 4/2018 ........... A61H 1/0274 |

* cited by examiner

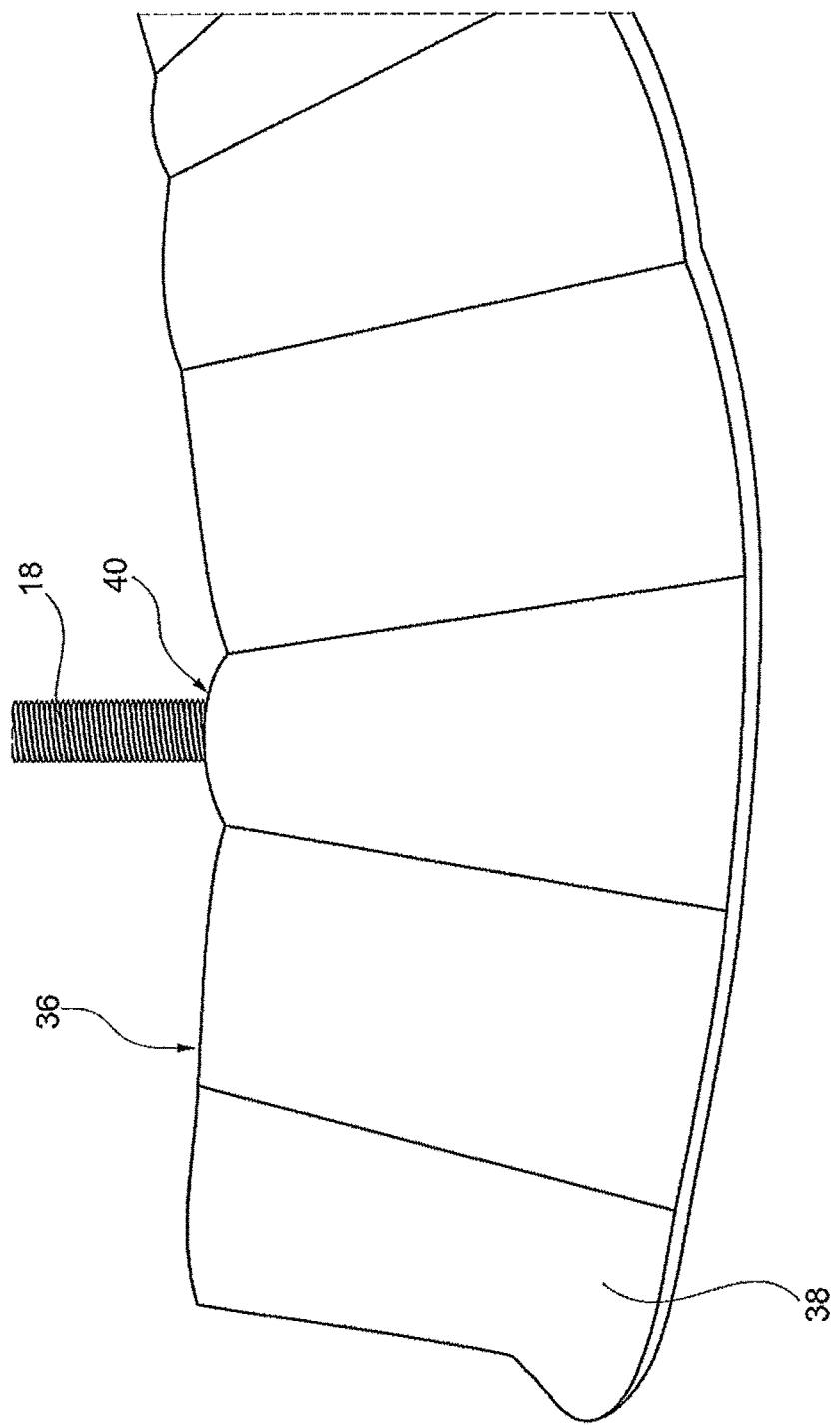

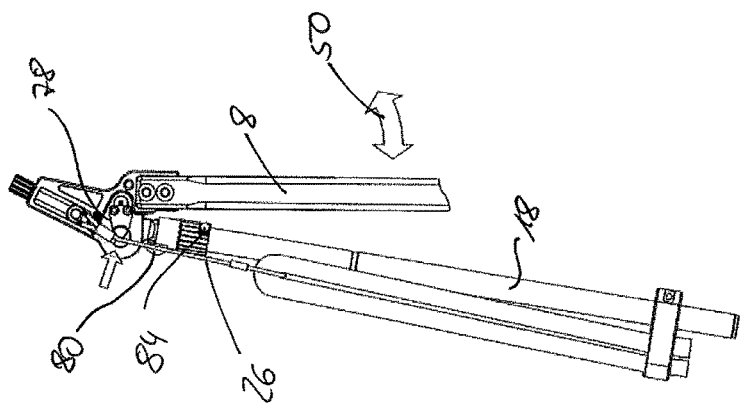
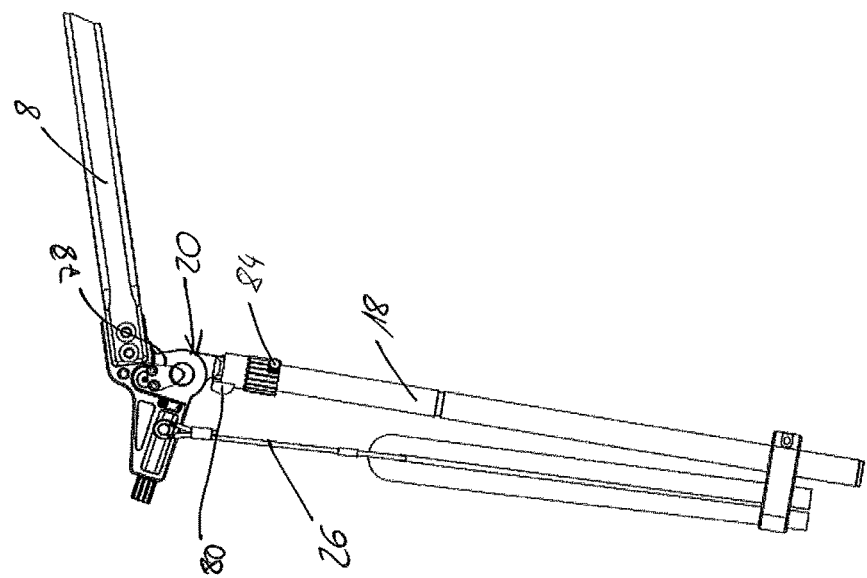
Fig. 22

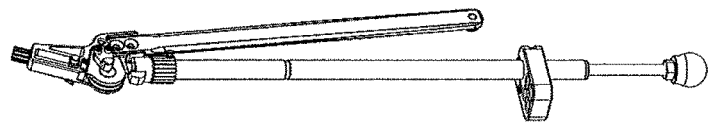
Fig. 23
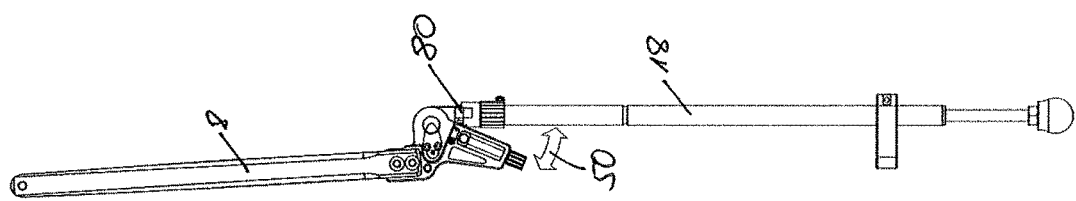
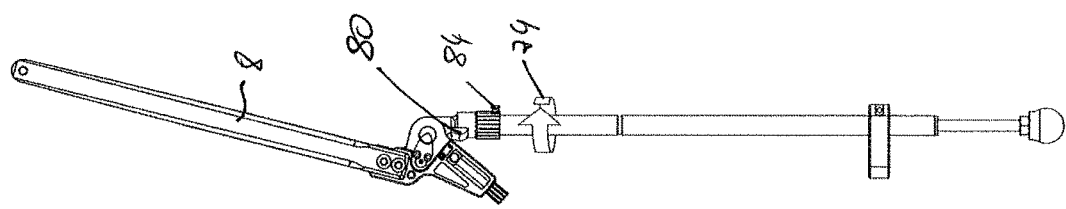
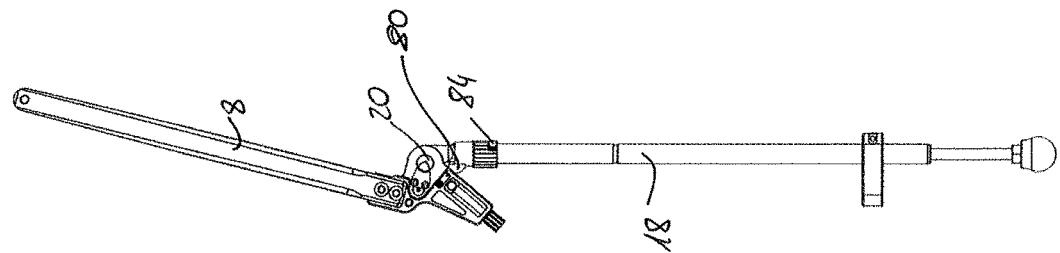

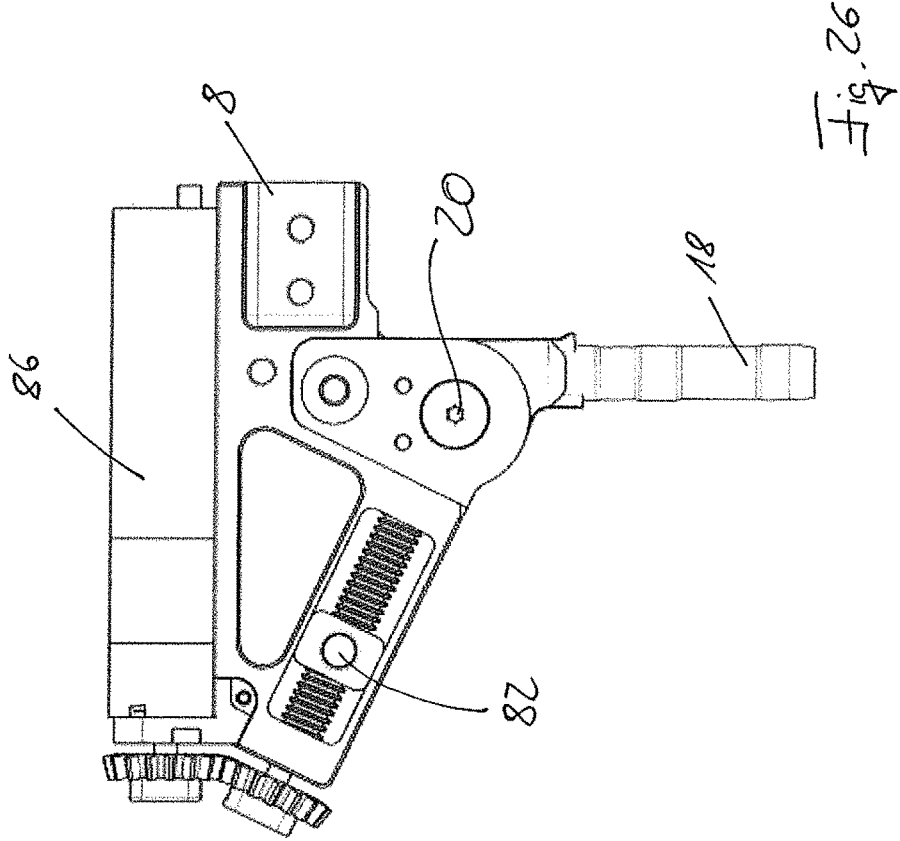

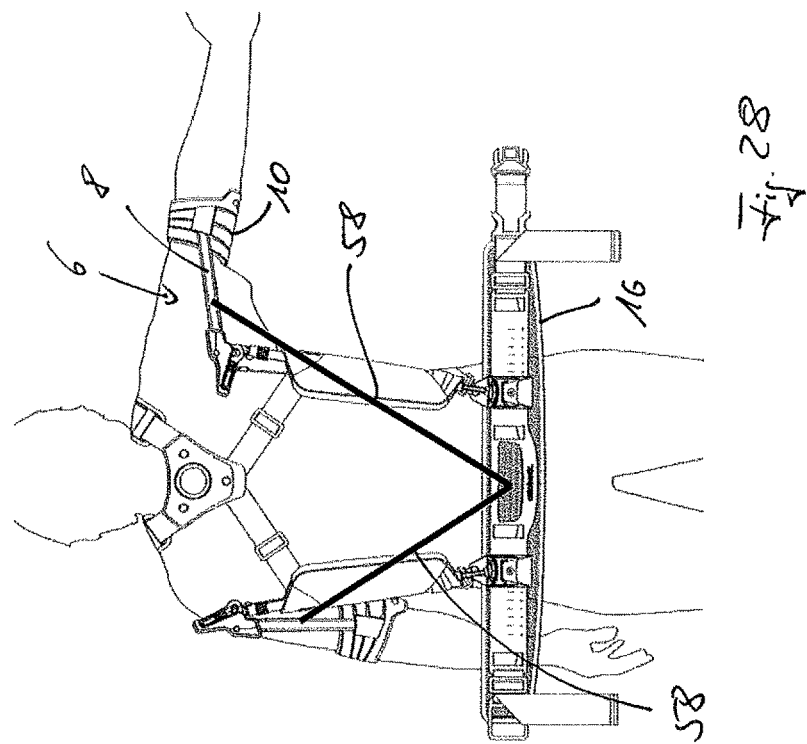
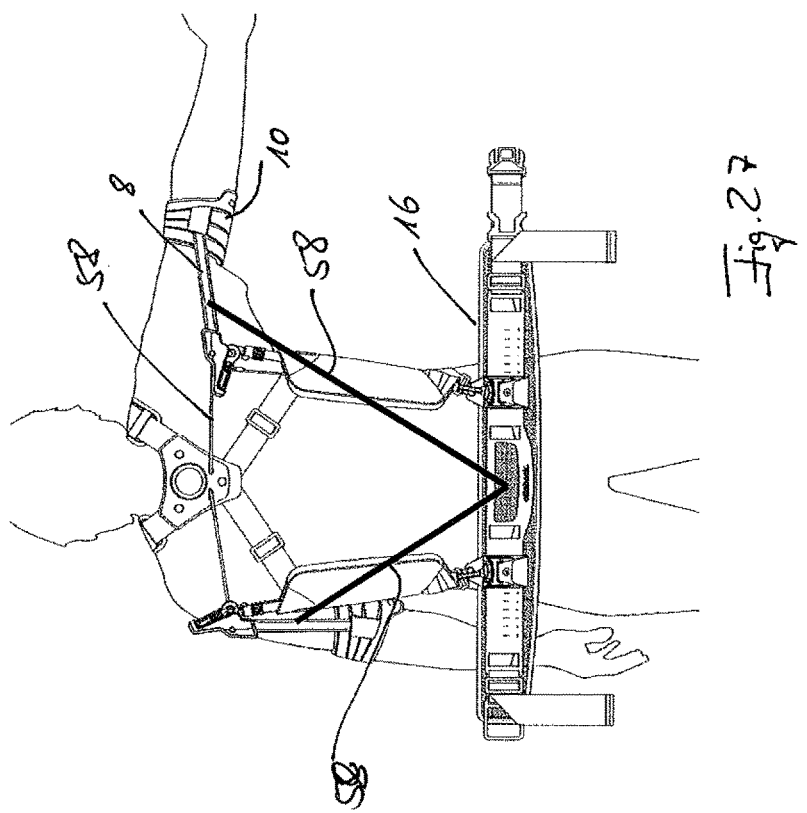

DEVICE FOR SUPPORTING BOTH ARMS OF A USER

The invention relates to a device for supporting two arms of a user, wherein the device has two arm support elements, each of which has an arm shell for placing on the arm, at least one passive actuator that is configured to apply a force on at least one of the arm support elements and at least one counter bearing for the force to be applied, which features at least one counter bearing element and at least two force transmission elements that are configured to transmit a counter-force from one of the arm support elements to the counter bearing element.

This type of device is described, for instance, in US 2016/0081871 A1. It features a counter bearing element that is designed in the form of a strap that can be placed around torso of the user. Two support braces run along the user's back to his shoulder, each of said support braces being connected to a joint above and laterally next to the shoulder of the user, such that the arm can be raised. Spring elements are arranged on the corresponding joints, by means of which an upward force can be exerted on the arm shells, such that the arms can be supported, for example when lifting heavy objects or when working above one's head. If the arms are lowered, a pressure must be exerted by the arms onto the arm shells, wherein this pressure exceeds the force applied by the spring elements, thereby causing the arms to lower.

WO 2014/093408 A2 and U.S. Pat. No. 9,427,865 B2 describe a similar device, each of which features a spring, especially a tension spring, that is connected to a Bowden cable, said spring functioning as a mechanical energy storage device which acts a passive actuator. The Bowden cable is guided by way of a pulley in such a way that, upon a swivelling of an arm, meaning a movement of the arm support element relative to the counter bearing element, the spring is stretched, such that the mechanical energy storage device is charged with energy.

In particular, if the user of the device trips or falls for instance and has to roll over, for example, these types of device may be hazardous for the user and lead to injuries.

This may occur even though the joints of the device that are arranged outside of the shoulder joint are, according to the prior art, arranged as precisely as possible so that their joint axes and swivel axes pass through the corresponding axis of the shoulder joint, such that supposedly all movements that the natural shoulder and hence the arm of the user can execute can be imitated.

An active device that supports arms while work is being performed above a user's head is described in EP 3 156 193 A1. The arm shells are connected to one another by a number of different joints and connecting frame elements. This should render as many movements as possible which are executable by a shoulder joint also possible with the mounted device. However, due to the number of elements, the device is large, structurally intricate and therefore expensive. It must also be noted that the device tries to imitate the shoulder joint by way of two hinge joints. This means that not all movements that a natural shoulder joint can carry out are possible. In particular, when it comes to raising the arm in a specific direction, the joint that is to conduct the movement must first of all be moved into the right position so its swivel axis points in the desired direction. This may require the execution of additional and unnatural movements, which reduce the user's level of comfort and therefore also his acceptance of the device.

Further support devices, especially devices which support the lifting of heavy objects or work performed above a user's head, are known from WO 2014/195373 A1 and US 2016/339582 A1. However, these devices are only intended for specific movements for which support is deemed necessary.

The invention thus aims to remedy these disadvantages or at least to reduce them.

The invention solves the task at hand by means of a device according to the generic term in claim 1, characterized by the fact that the force transmission elements are arranged on the counter bearing element such that they can be moved relative to the counter bearing element, in particular they can be rotated about at least one rotational axis. To this end, the force transmission elements can be fixed to the counter bearing element by way of a hinge, a ball joint or another joint for instance, or for example plugged or inserted at one end of the force transmission element into a pocket or bracket on the counter bearing element specifically provided for that purpose.

The invention is based on the knowledge that, in spite of the often complex and intricate arrangement of joints, such orthoses and devices are not capable of imitating many movements in the shoulder region of the wearer. This applies especially to movements during which the orientation and/or position of the at least one arm support element relative to the counter bearing element changes, and which are not or not only caused by a movement of the shoulder, but for example by movements of the torso, the spine or the shoulder girdle. In the situations described, in which the user trips or falls, these movements are of particular importance with regards to breaking the fall and avoiding injury.

In particular, it is based on the knowledge that, for the device described in EP 3 156 193 A1, the hinge joints require a fixed reference point to the anatomical joints and the pivot points are thus firmly fixed by the frame.

The movability of the force transmission elements relative to the counter bearing element means that, in a preferred configuration of the device, the freedom of movement of at least one of the arms, preferably both arms, is not restricted by the device.

Within the scope of the present invention, the notion that the freedom of movement of the arm is not restricted by the device should be understood especially to mean that every movement which the user of the device can execute without a device is also possible with the device; the user is therefore restricted to, at most, a minimal degree, i.e. not significantly. In particular, these movements include anteversion and retroversion, i.e. the raising of the arm forwards and backwards, abduction and adduction, i.e. the raising and lowering of the arm in a lateral direction, and the internal and external rotation in the shoulder joint. In particular, a device according to the invention renders possible a circumduction to the same degree as can be performed by the person without the device. A circumduction is the circular movement of the arm about the primary executable movements of the three joint axes, in particular at maximal movement deflection, which results in an irregular cone, the tip of which lies in the shoulder joint.

Movements of the spine, particularly a leaning of the spine to the side and/or forwards and backwards and/or a twisting of the spine about its longitudinal axis, are preferably not prevented, restricted or rendered impossible by the device either. All of the movements described here are preferably restricted by the device in neither their maximum movement deflection nor in a sequence of movement.

In this case, the arm shell can be moved in at least three translational and three rotational degrees of freedom in relation to the at least one counter bearing element. While devices known from the prior art allow at most rotational degrees of freedom, the device according to the invention also enables movements of the arm shell relative to the counter bearing element, such movements comprising solely a translational movement along a direction in space, for example. As a result, the arm shell can trace and perform movements of the upper arm relative to the counter bearing element, wherein these movements are not only the result of movements of the shoulder, but also require a movement of, for example, the spine or another body part.

In a preferred configuration of the device according to the invention described here, the force transmission element features a compression force transmission element, especially a rod or a splint, on which the arm support element is arranged such that it can be swivelled about a swivel axis. In this case, it is often sufficient to provide a single hinge joint with a swivel axis. Complicated structures comprising several joints, whose swivel axes meet at a point, preferably virtually at the pivot point of the ball joint of the natural shoulder, are not necessary. This considerably simplifies the structure and allows for a reduction in production costs.

When the device is in the mounted state, the joint, by means of the which the arm support element is connected to the force transmission element, is preferably located in a shoulder blade region, preferably on the shoulder blade, of the user. However, this does not mean that the joint, when mounted, is in contact with the body of the user; rather, this contact would only occur on the user's shoulder blade if the joint were to be pressed onto the user's body.

During operation of the device, the counter bearing device is placed on an object to which the acting force should be transmitted. Given that the passive actuator is to apply a force on the arm support element, a corresponding counter bearing must be provided on which it can be supported. A passive actuator within the meaning of the present invention is specifically not a motor. The required energy it needs to apply the force is produced by the user or wearer of the device. Generally speaking, the force that is to be applied to the arm support element counteracts the force of gravity. When the arm and the connected arm support element are raised, energy is withdrawn from an energy storage device of the passive actuator. When the opposite movement is executed, i.e. a lowering of the arm, this occurs against the applied force. The energy storage device of the passive actuator is supplied with energy. For a passive actuator within the meaning of the present invention, this is the only source of energy when an adjustable preload of the energy storage device of the passive actuator does not occur.

The passive actuator preferably features at least one energy storage system, preferably at least one mechanical energy storage system. For instance, this may comprise a spring element, a pressure accumulator, a pneumatic and/or hydraulic system and/or a hydraulic energy storage system. The spring element, for example, may be arranged directly on the joint between the compressive force transfer element and the arm support element in the form of a rotational spring or a constant force spring. Elastic elements in the form of elastic cables, such as rubber cables, are also conceivable, one end of which is arranged on a part of the arm support element. If the arm support element is swivelled about the swivel axis relative to the compressive force transfer element, the elastic element is stretched or compressed, such that energy is either supplied to or withdrawn from the mechanical energy storage system. Of course, other elements, such as gas springs or compression springs, are also conceivable, for which a deflection is used to transform the compressive force coming from the compression spring into a tensile force.

The mechanical energy storage system may be arranged at various positions on the device. Preferably, a position is selected at which the installation space required for the energy storage device is available and the energy storage device does not cause any disruption, even while the user's arm is moving. Accordingly, it may be arranged on the upper arm, for instance.

In a preferred configuration, the counter bearing element is a mounting element, especially a strap, a belt, a bandage or a shell element, for placing the device on a body part, in particular a torso of the user. The mounting element is preferably integrated into an item of clothing, such as a pair of trousers. Alternatively or additionally, the counter bearing element comprises at least one shoulder element for placing the device on a shoulder of the user. Alternatively or additionally, the counter bearing element has at least one ground contact element, thereby enabling the counter force to be introduced into the ground. Such ground contact elements are preferably designed as exoskeletons and are known from the prior art. It may be designed to be active, for instance motor-driven, or passive.

If the counter bearing element is designed as a mounting element for the user's torso, especially the user's hips, the required counterforce can be diverted in a way that is particularly comfortable and convenient for the user. It is introduced into the body of the user via the hip region and absorbed by the legs. The deployment of a ground contact element is especially advantageous if the device is used to support during the lifting of heavy loads. In this case, were the counter bearing element designed as a mounting element for the torso, especially the hips, of the user, the additional strain caused by the heavy load would indeed be diverted by the shoulder region of the user; however, this would have to continue through the legs. This can be remedied via the use of at least one ground contact element. In this case, it is possible to divert at least part of the strain, yet preferably the complete additional strain, into the ground, the result being that the user's legs and in particular his knees are not over-burdened. To this end, orthoses such as active or passive exoskeletons, the principle of which is known from the prior art, can be used, wherein these orthoses extend from the hips, via the knee and the ankle, down to the user's foot.

The use of a shoulder element for placing on the shoulder, which may be configured in the form of backpack straps or suspenders for example, allows for an especially small construction of the device. However, it does have the disadvantage that the forces that are actually to be diverted from the shoulder region are actually introduced into the shoulder region at another point, thereby reducing the effect compared with the use of another counter bearing element. Of course, the counter bearing element may also be a flexible or rigid element that is to be arranged on the shoulder or another part of the human body, in particular another part of the user's torso.

It has been proven to be advantageous if the orientation of the force transmission element can be changed relative to the counter bearing element by way of a movement of the torso and/or a movement of the arm of the user. As a result of this change in orientation, such as a change in a direction of longitudinal extension or an angular position of the force transmission element relative to the counter bearing element, it is possible to realize a number of movements and degrees of freedom, preferably all movements and degrees of freedom, which cannot be achieved by the swivelling arrangement of the arm support element on the compressive force transmission element. The fact that the change in orientation is achieved simply by a movement of the torso and/or arm of the user ensures an intuitive operation of the device. The compressive force transmission element is preferably connected to the mounting element by means of a joint, especially a ball joint or a hinge. The exact configuration of this joint depends on its intended purpose and the circumstances, in particular the individual preferences of the user. A ball joint may be used which enables a swivelling of the compressive force transmission device, which is designed as a rod or a pole for example, relative to the mounting element, which is designed as a belt or a strap for example. This type of joint may also allow for a torsion, i.e. a rotation of the compressive force transmission element about its own longitudinal axis. However, where applicable, the provision of a simple hinge joint shall suffice, the compressive force transmission device being arranged on the attachment element via said hinge joint. In particular, this shall suffice if the mounting element is so flexible that it still enables a movement of the compressive force transmission element relative to the mounting element, this movement resulting in a deformation of the mounting element. Given that the mounting element itself is designed to be a flexible element, this deformation is reversed upon a corresponding movement of the user's arm and/or torso. As a result, at this point, as simple a connection as possible between the compressive force transmission device and the mounting element is achieved.

The joint, via which the compressive force transmission device is arranged on the arm support element, may be designed in a different way. It may be designed as a prismatic joint or chain joint, or as a folding mechanism. Elastic elements, such as bending springs, may also be used a joints and at least also as a mechanical energy storage device at the same time. Of course, the Bowden cable principle, for instance in the form of a push-pull cable, can also be used.

The arm support element comprises the arm shells that are preferably arranged on a spacer element. This spacer element, as part of the arm support element, is preferably connected to the compressive force transmission element or the force transmission element. The lengths of the compressive force transmission element, which is designed as a splint or rod for example, and where applicable of the spacer element, which is designed as a rod or splint, are preferably selected such that the entire angular range of the potential movement of the upper arm of the wearer is covered. The arm shell is preferably flexibly arranged on the spacer element to render the device as comfortable as possible to wear.

In a preferred configuration, the passive actuator is configured to apply the force depending on a position and/or orientation of the at least one arm support element relative to the counter bearing element, especially depending on a swivel angel of the arm support element about the swivel axis, wherein the passive actuator preferably applies the force to the arm support element eccentrically. The force is preferably applied to the spacer element of the arm support element. Instead of using, for example, a constant force spring as a passive actuator, by means of which the same force is always applied regardless of the position and angular position of the upper arm and thus also of the arm support element, passive actuators may be used by means of which different forces may be applied depending on the position and/or orientation of the arm and thus the arm support element. In this way, it is advantageous, for instance, to not apply a force so long as the arm does not exceed a certain angle relative to the normal, i.e. the direction that follows the laws of gravity. This angle may be 45°, 60° or 90°, for example. Only when the arm is raised beyond this angle is a force preferably applied by the passive actuator, said force counteracting the force of gravity. This force may vary with the continued raising, i.e. swivelling, of the upper arm and thus the arm support element relative to the compressive force transfer element. To this end, cam discs, gears or other force-path-functions, such as slots, may be used. A maximum force is preferably applied within an angular range of 70° to 120°, especially preferably at 90°.

Preferably, the force that can be applied by the passive actuator can be altered by way of an alterable preload of the passive actuator and/or an adjustable eccentricity of the application of force on the arm support element.

In a preferred configuration, the force transmission element is mounted in a guide which prevents the part of the force transmission element on which the arm support element is arranged from moving away from the user's torso when the device is mounted. In a structurally particularly simple configuration, the guide refers to a loop or a sleeve that is preferably made of a fabric. The guide preferably serves as a positioning aid. A movement of the force transmission element relative to the guide is beneficial but not necessary.

It is especially preferable if the device features two arm support elements for supporting both arms, wherein each of the two arm support elements has an arm shell and is preferably arranged on a force transmission element such that it can be swivelled, and wherein at least one connection element, especially a tension element, is preferably arranged between the force transmission elements, by means of which a tensile force can be preferably applied to both force transmission elements. This also prevents the end of the force transmission elements facing away from the counter bearing from moving too far away from the body, especially the torso, of the user. Furthermore, the arm shell is preferably held in place on the arm of the user by such a tension element, thereby largely or completely preventing a displacement.

In particular, if two arm support elements and two force transmission elements are provided, these may also be arranged in two-dimensional layers, for instance in the shape of a cross. It is also possible to use several supports or springs, elastic or mechanical energy storage devices or other force transmission or force application elements. The two-dimensional arrangement means that, when in the mounted state, the device is not particularly bulky and is thereby less disruptive during day-to-day activity. Moreover, it enables the force transmission elements to more easily follow the movements of the user's torso.

The device can preferably be adjusted to fit different physical dimensions of the user. As a result, the device is versatile and flexible; there is also no need to provide different devices for users with varying physical dimensions. For example, the length of the force transmission element, especially in the form of the compressive force transmission element, can be adjusted by way of telescopic rods, for instance. These may comprise quick-release levers or swivel locks, rendering an unlocking, adjustment of length and subsequent locking very easy. This is preferably provided in an infinitely variable configuration. However, it is also possible to provide separate grades of adjustment. For instance, locking bores may be provided with which a pin—which is spring-loaded from within—engages when the desired length has been set. In order to adjust the length, the pin is pushed into the telescopic rod and the numerous elements of the telescopic rod are shifted relative to one another.

Of course, the length of the spacer element of the arm support element can also be adjusted in the same way. A telescope or a telescopic rod can also be used for this purpose. Alternatively or additionally, the arm shell may be designed to slide on or in the spacer element in order to compensate for incongruencies. In this case, certain movements of the upper arm relative to the shoulder result in a movement of the arm shell relative to the distance element, such that the arm shell always comes into contact with the arm of the user in the same region.

Alternatively to a telescope, inter-twisted spirals or pivot bearings on the upper arm can be used to set the length and direction.

The joint, by means of which the force transmission element is arranged on the mounting element, is preferably securely mounted on each mounting element. If said element is designed to be a strap or a belt, its length is easily adjusted, meaning that the position of the joint is also easily adjusted. Alternatively or additionally, the joint—which may be designed as a clip for example—can also be connected or is connected to the mounting element such that it is detachable. Alternatively or additionally, it may be configured in such a way that it can be shifted along a splint, a slot or another contour. Other possibilities include the arrangement inside a belt pouch, the coupling of the joint via a so-called ratchet closure, as is common with ski boots for example, as a pin fastener or via a velcro fastener.

It is especially easy to identify the right size of the device if the device is integrated into an item of clothing, especially a jacket or a shirt. In particular, the mounting element is preferably integrated into a pair of trousers. In this case, only the user's clothing size need be identified for items of clothing in the right size to be selected.

Given that forces of various strength must be applied by the actuator for users of varying size and strength, it has been proven advantageous if the strength of the force to be applied is adjustable. This may be achieved, for example, by ensuring that a preload of a spring element, such as a coil spring, can be adjusted via a rotating dial or a sliding mechanism, for instance. The length of a slackened spring, i.e. the length of the spring without a load, is also adjustable. Alternatively or additionally, several coils or spring elements may be provided that can be activated either individually or collectively, and which may—but do not necessarily have to—feature different spring constants and degrees of hardness. The length of a lever arm, which is subjected to the force applied by the passive actuator on the arm support element, especially on the spacer element of the arm support element, can also be adjusted and, for example, altered by way of a setscrew. The same applies for the end stop of a Bowden cable. The setting may be executed mechanically or mechatronically, for instance by way of a motor. The mechatronic adjustability is advantageous, for example, if the applicable force is to be adaptively adjustable, such as if a greater supporting force is required or desired because an item, such as a tool, is being held.

It has been proven especially convenient if the spring elements and the other mechanic, hydraulic or pneumatic energy storage devices are not tensioned until the device is mounted. They can also be slackened upon removal of the device. This may occur, for instance, by way of levers, loops or detachable clamping connections which are connected to the respective spring elements and, where applicable, allow for a tensioning of the spring to the desired degree. Alternatively or additionally, slides may be provided on which one end of the spring element is arranged, for example. By moving the slider along a guide element, the spring or the spring element can be tensioned or slackened. The locking and fixing in a particular position is preferably achieved by tilting the slide on the guide element.

It is especially preferably if the arm shell is a self-closing shell, which is open so long there is no arm inside it. If the arm is introduced into the shell, an activation mechanism is triggered which causes to shell to close. This mechanism can also be used to tension the spring elements.

The device preferably has a blocking device, by means of which a movement of the arm support element relative to the force transmission element can be blocked in at least one direction; preferably, the movement can be blocked completely.

At least one tension element, in particular at least one tension spring, is preferably situated between the arm support elements (translator's note: the original contains an assumed typo; 'Anstützelemente' rather than 'Armstützelemente'). As a result, a tensile force is exerted on each of the arm support elements that acts in the direction of the respective other arm support element. Surprisingly, this ensures that the force transmission elements do not move away from the torso of the wearer, even if the wearer of the device carries out complicated or unusual movements. This reduces the risk of components of the device hitting other objects or door frames for example, which would reduce the wearer's acceptance of the device.

Preferably, at least one of the arm shells, but preferably both arm shells, features a fastening element, especially one that is designed as a strap. This fastening element is used to secure the arm shell around the arm. For instance, the strap can be wrapped around the arm and fixed at an opposite end of the arm shell by way of a fixing element that can be arranged at a free end of the strap and designed as a velcro fastener, for example. Of course, there are other ways to fix it, such as a clasp, a positive form locking element, for example in the form of a button, or other fastening elements.

The fastening element can preferably be fixed to another element, other than the arm shell of the device, by means of at least one fixing element. This other element is preferably a shoulder strap or a force transmission element or a cladding for one of these force transmission elements or the counter bearing element. In this case, if the wearer of the device removes the device, he must first release the fastening element so as to be able to remove his arm from the arm shell. Generally, at this point there is a risk that the removal of the arm from the arm shell will lead to a reduction in the force applied to the arm support element by the arm, while the force applied by the passive actuator remains available. This may result in a rapid, for example jerky, upward movement of the arm support element, which may result in injury or damage to equipment or objects in the surrounding area. However, if the arm shell is locked by way of the fastening element, the fastening element must first of all be released in order to remove the arm from the arm shell. The wearer of the device thus holds one end of the fastening element in his hand, the result being that a downward acting force continues to act on the arm shell and therefore also the arm support element. In this case, the fastening element is preferably arranged on a different element of the device, such as a shoulder strap. This enables the control of the device and, where appropriate, allows it to be brought slowly into a type of "parked position" without the occurrence of any jerky movements.

The reverse is carried out when mounting the device. The wearer of the device who wishes to mount the device must first of all release the fastening element from the other element of the device, thereby already applying a force on the arm support element in order to bring it in the desired position ready for mounting. In doing so, it is preferable if he does not let go of the fastening element until the arm is in the arm shell. The fastening element is then closed around the arm and the device is securely mounted.

The device preferably has an end stop, by way of which a movement of the arm support element relative to the force transmission element about the swivel axis is restricted. The device preferably comprises two end stops, each of which restricts the movement of an arm support element about the swivel axis relative to the respective force transmission element. This prevents an overshooting of the various structural components relative to one another, for example if the verticals are surpassed.

The end stop can preferably be moved into an active position, in which it restricts the movement, and a passive position, in which it does not restrict the position.

This is preferably achieved by the end stop being a projection on the force transmission element. In this case, the force transmission element is simply rotated about its longitudinal axis in order to bring the projection into the active or passive position.

The counter bearing element preferably features a strap which can be fastened by way of a fastener and that can be wrapped around a torso of the wearer. Such a strap constitutes a stand-alone invention and can be used on its own or as part of such a device, in particular as part of an orthosis or a prosthesis. In this way, such a strap can also be wrapped around a different body part of a wearer of the device or around an object. Such a strap is always advantageous, for instance, if the strap, when closed, is subject to such tension that an inadvertent opening of the strap would lead to a jerky and uncontrollable release of this tension. This refers to a hip or abdominal strap, for example. Here, the fastener is designed in such a way that it requires at least two steps to open and close it. For example, if a simple snap fastener were to be used as a fastener which can be released, for instance, by activating one or two activation elements, there is a risk that, as a result of the forces acting by way of the actuators, the ends of the strap would rapidly move apart, thereby hitting any objects or persons in the surrounding area. The fastener is designed to feature two steps in its operation to avoid such a situation.

One end of the strap is preferably guided through a loop arranged at the other end before a positive-locking fit of two correspondingly designed positive-locking elements is created to seal the fastener. In this case, it is preferable if one of the two positive-locking elements is arranged at the end that is guided through the loop. To open the fastener, the positive-locking fit must first of all be released, followed by the guiding of one of the ends of the strap through said loop, wherein the one positive-locking element is once again guided through the loop.

Preferably, the passive actuator features at least one elastic element and the device at least one mounting element which, at a predetermined angle between the arm support element and the force transmission element, fits closely on the elastic element, thereby changing the force that is to be applied to the arm support element. During a movement of the arm support element relative to the force transmission element, the elastic element exerts a force, as it is stretched or compressed. The support element is preferably mounted relative to the force transmission element such that is can be rotated and a point of application of the force applied by the elastic element lies eccentrically relative to the rotational axis of the corresponding joint. A swivelling of the arm support element relative to the force transmission element thus causes a change in the direction of the force applied by the elastic element. In particular, the mounting element, which is preferably arranged on the joint, is arranged such that it comes into contact with the elastic element at a predetermined angle. From this moment onwards, the force acting on the point of application is no longer determined by the direction between the point of application and the second bearing point of the elastic element, but rather by the direction between the point of application and the point at which the mounting element fits closely on the elastic element. If this point is located as close as possible to the rotational axis, preferably precisely on the rotational axis, the force that is applied by the part of the elastic element runs almost exactly or exactly axially, such that a torque is no longer exerted on the arm support element. This force can be adjusted by shifting or altering the position of the mounting element.

Therefore, it is preferable if the predetermined angle and/or the change in the force to be applied can be adjusted, preferably by ensuring that the mounting element can be shifted relative to the arm support element and/or the force transmission element. This may be achieved, for instance, by ensuring that the mounting element can be shifted in a slot and, for example, fixed by a screw.

Figure 5:
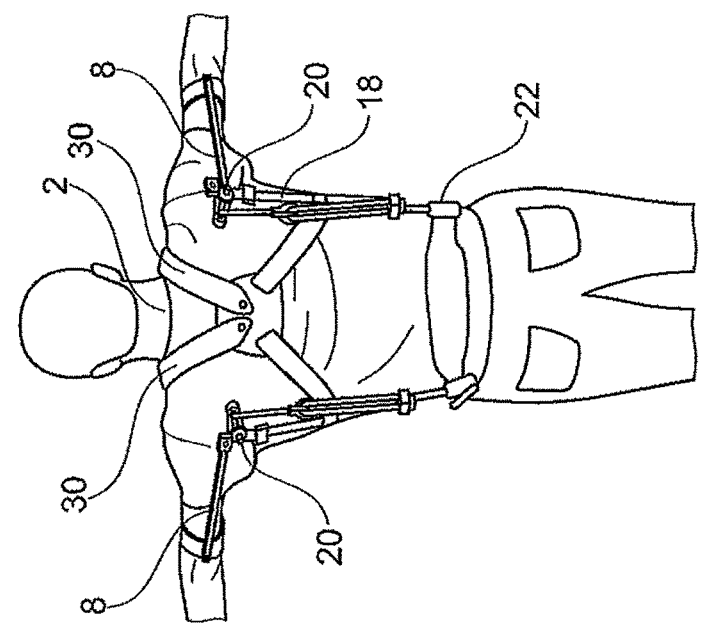
Figure 6:
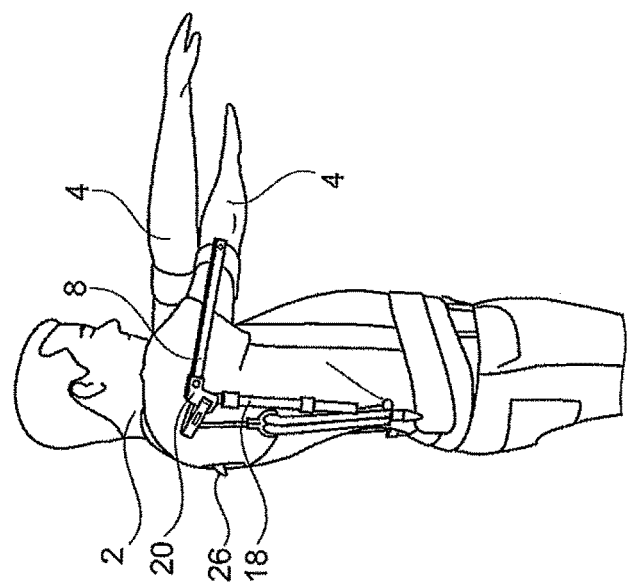
Figure 8:
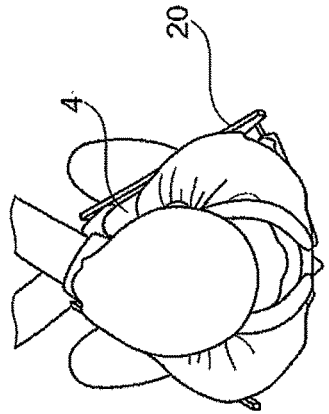
Figure 7:
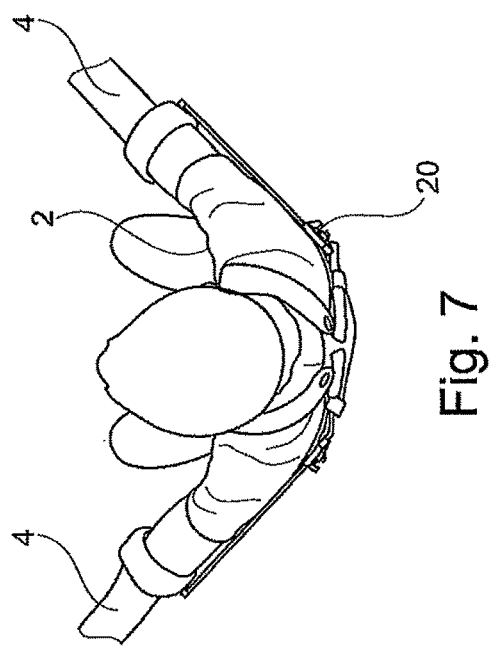
Figure 9:
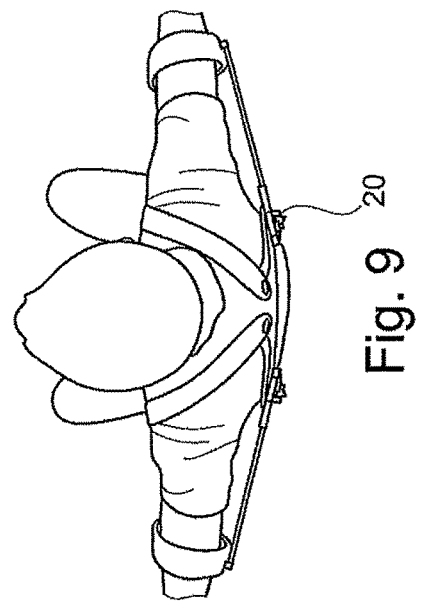
Figure 10:
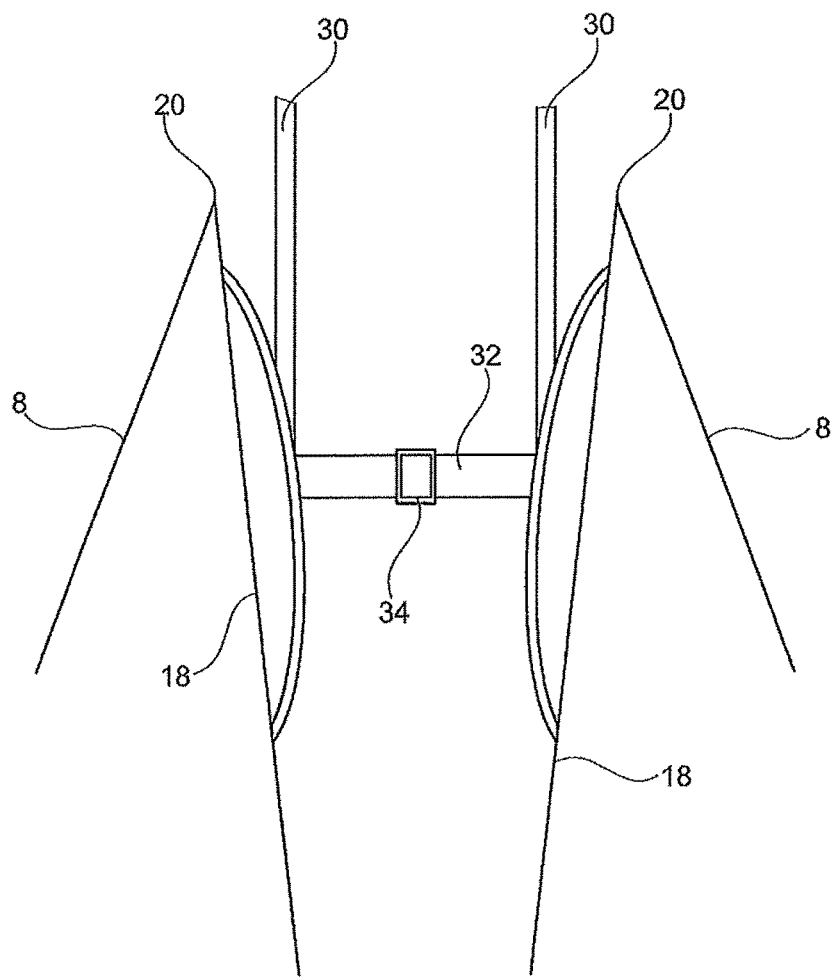
Figure 15:
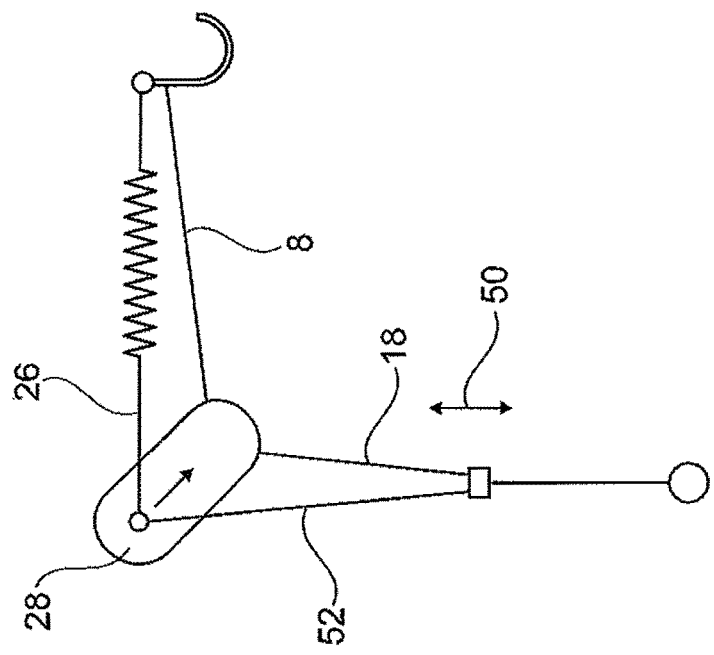
Figure 16:
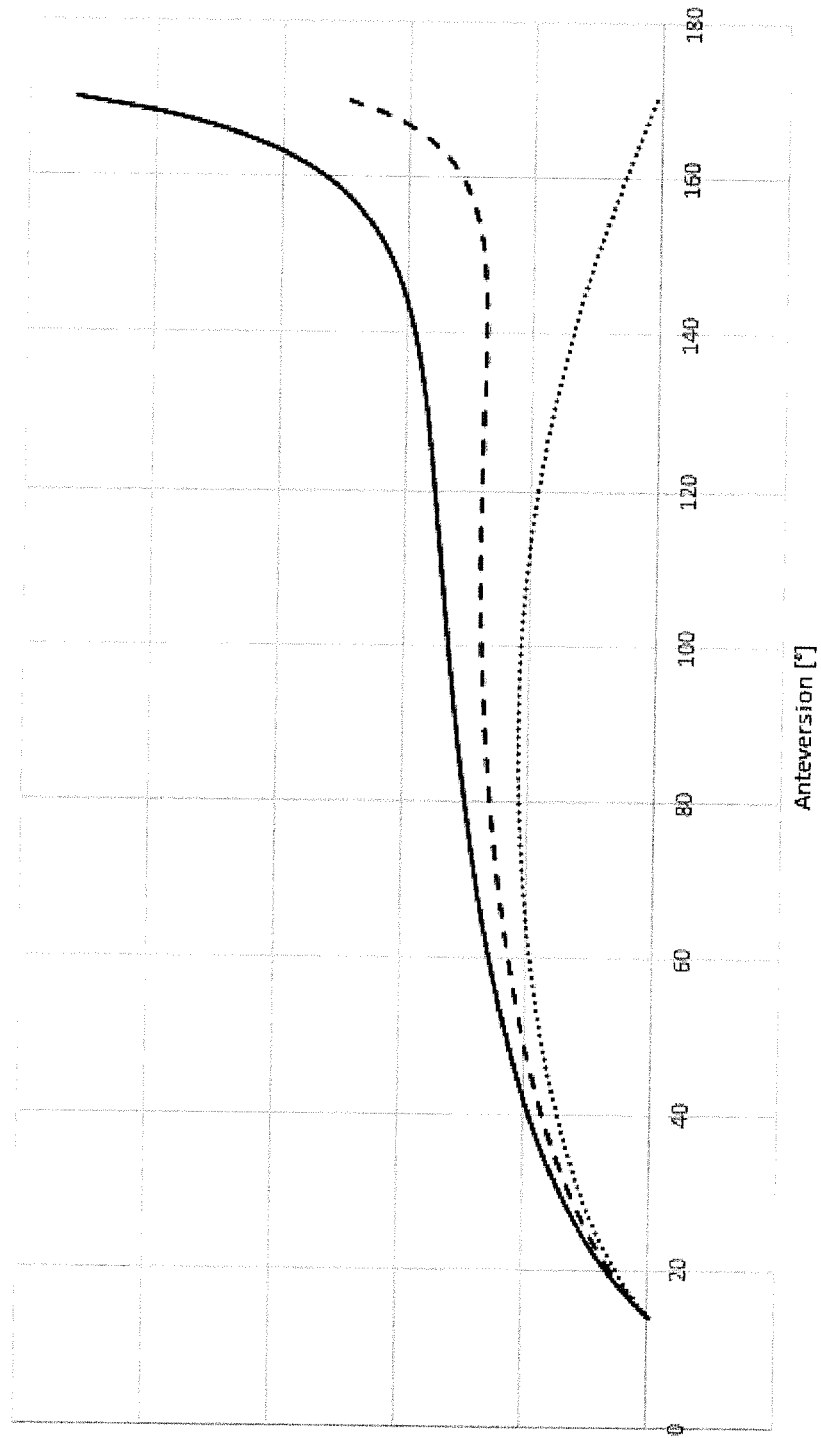
Figure 17:
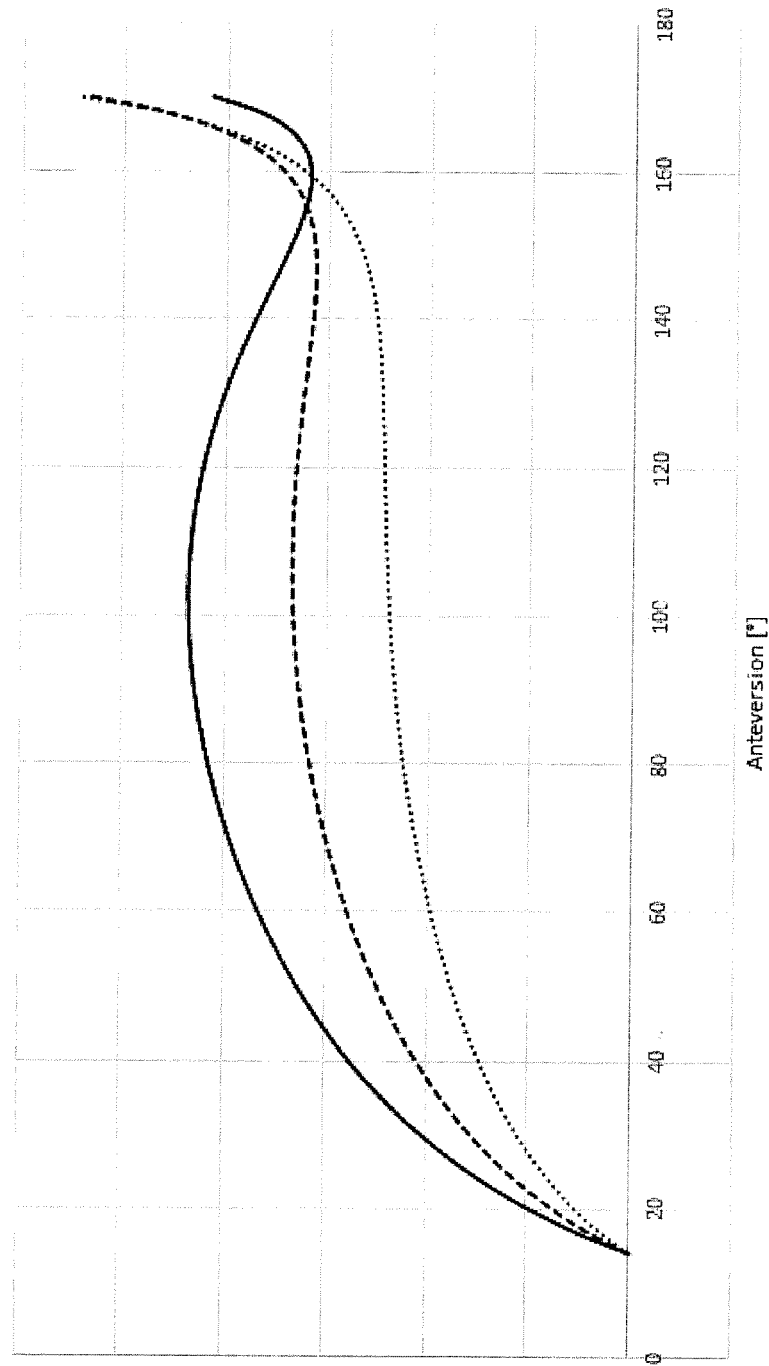
Figure 18:
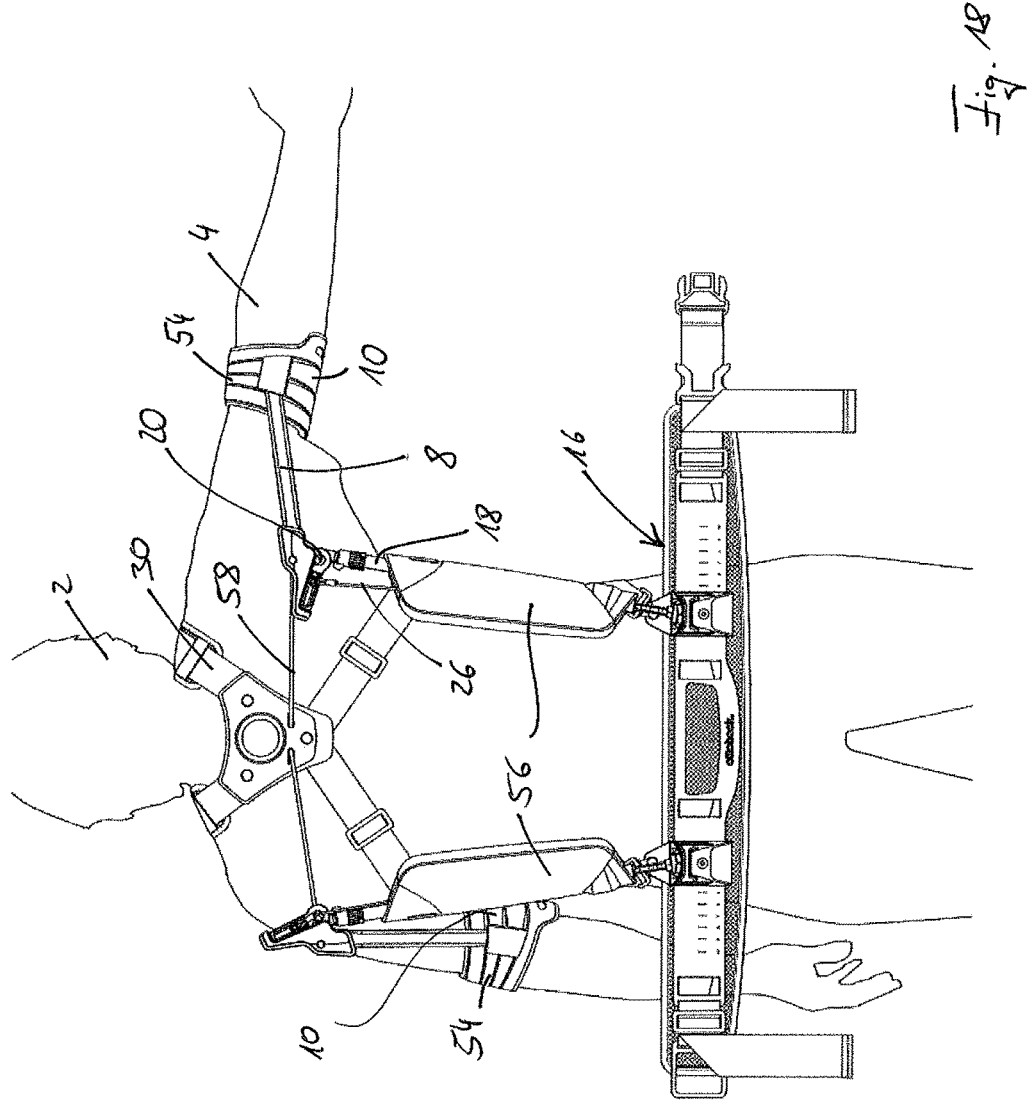
Figure 19:
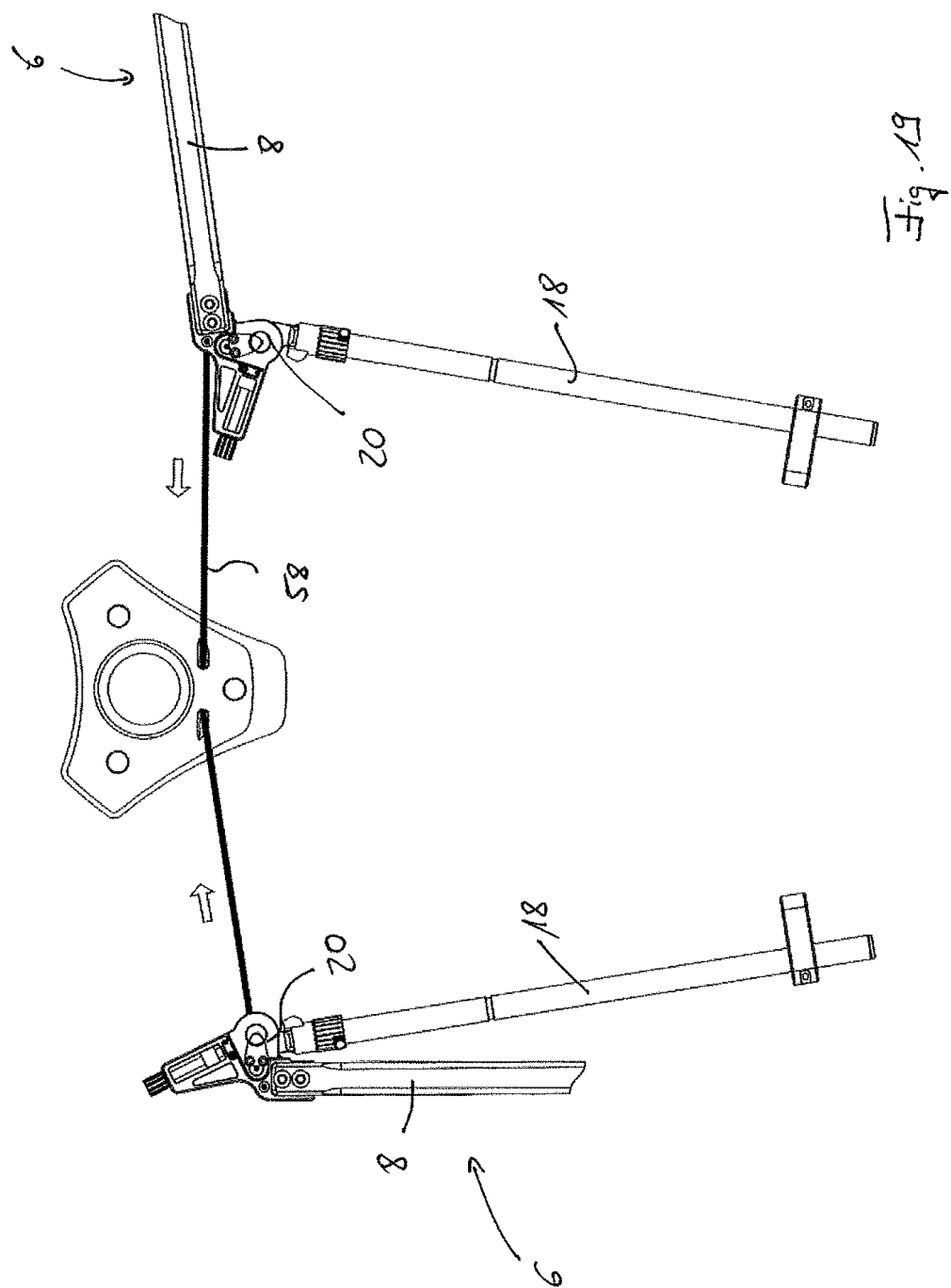
Figure 20:
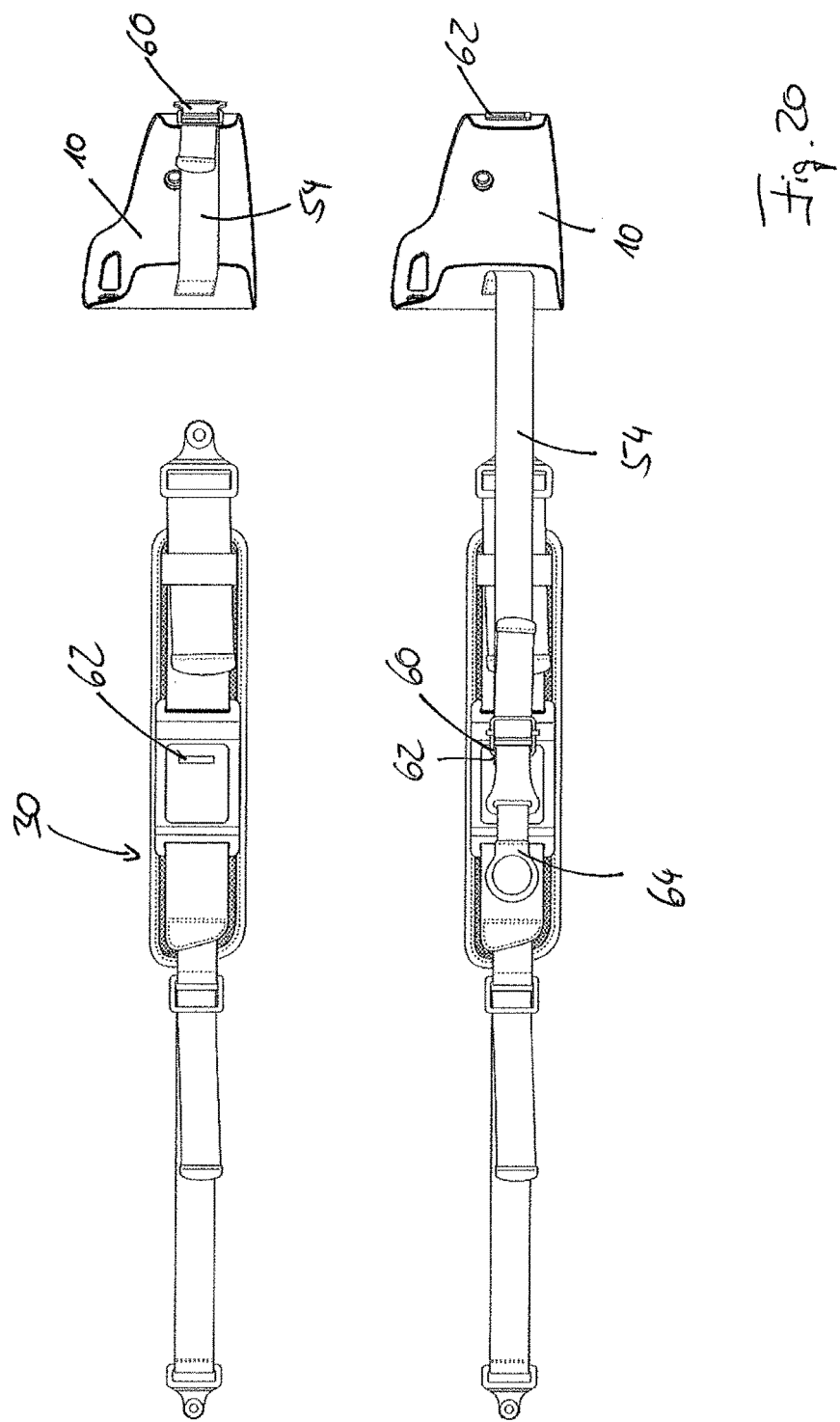
Figure 21:
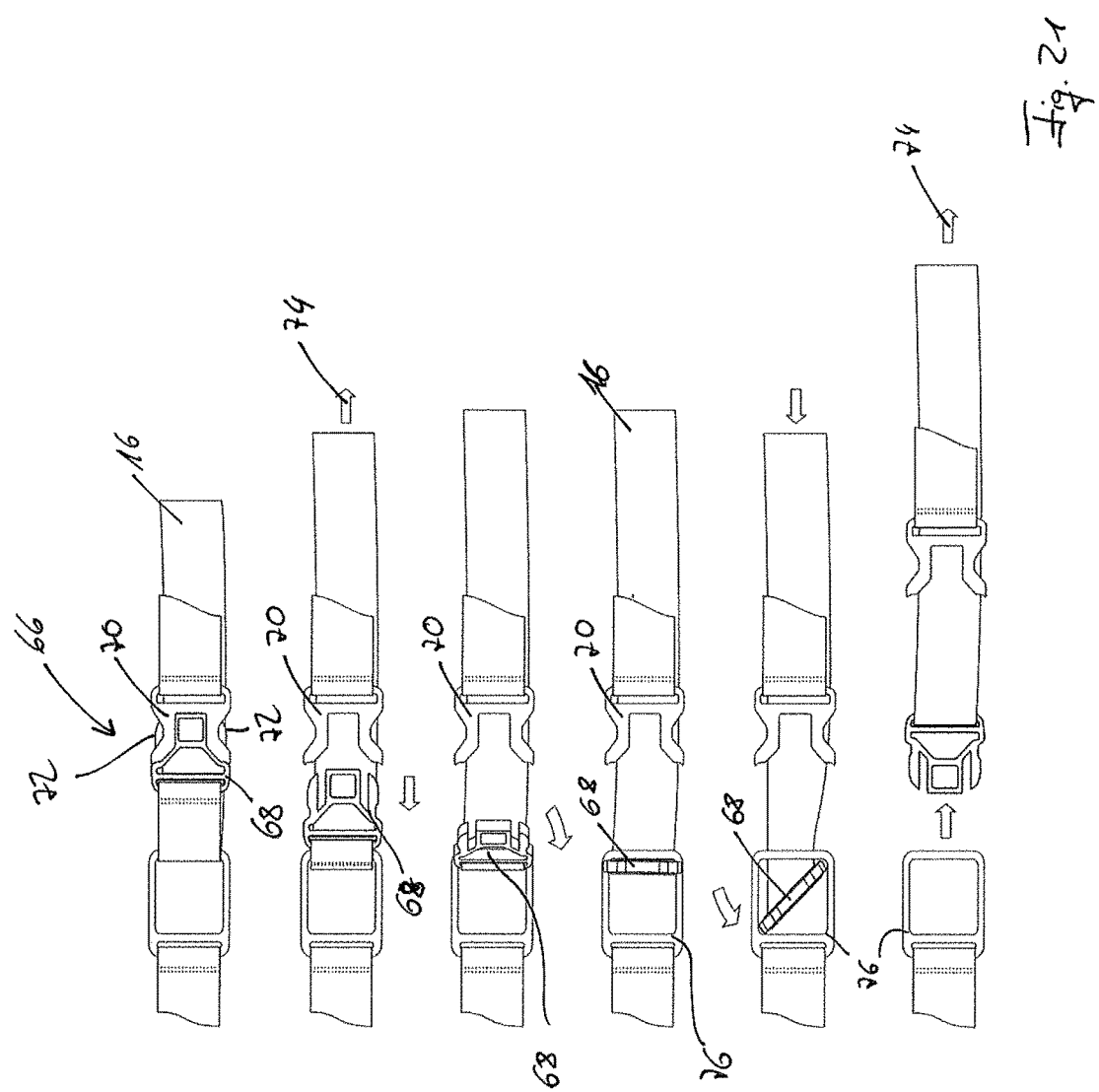
Figure 24:
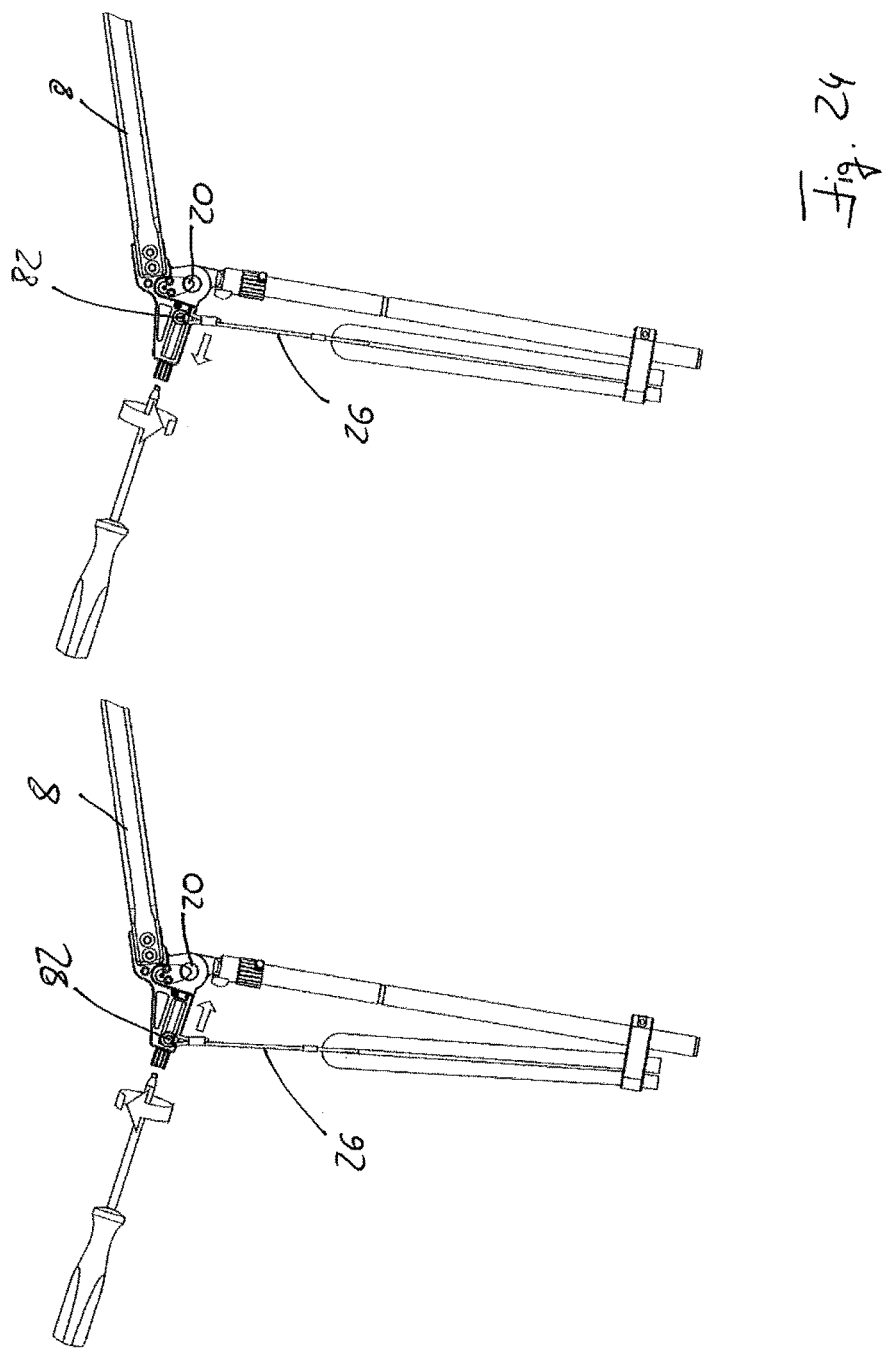
Figure 25:
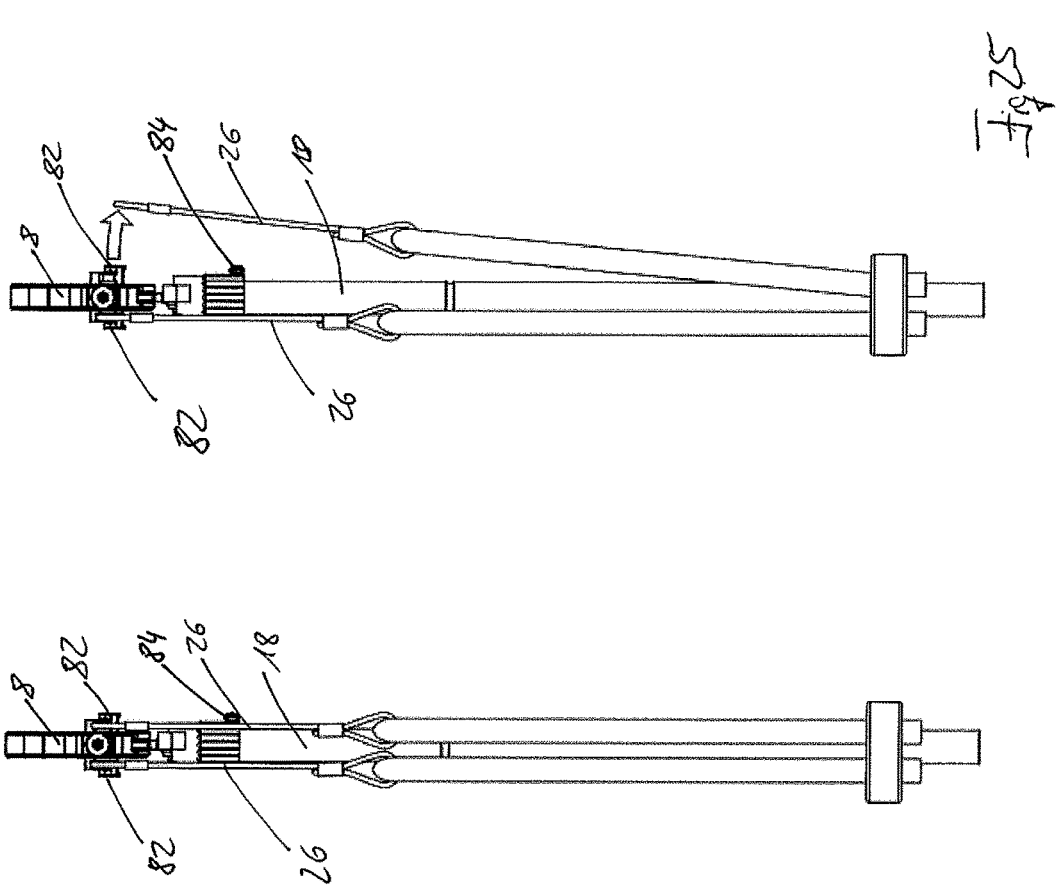

In the following, an example of an embodiment of the present invention will be explained in more detail by way of the attached drawings: They show:

FIG. 1—a schematic depiction of a device according to a first example of an embodiment of the present invention when in the mounted state, FIGS. 2-6—a depiction of a mounted device in various positions from a lateral perspective, FIGS. 7-9—depictions of a mounted device in a top view from above, FIG. 10—a schematic depiction of a device according to a further example of an embodiment of the present invention, FIG. 11—a schematic depiction of a section of a device, FIGS. 12-15—schematic depictions of devices according to further examples of an embodiment of the present invention, FIGS. 16 and 17—exemplary depictions of force patterns, FIG. 18—a schematic view of a mounted device, FIGS. 19 and 20—schematic depictions of individual elements of the device, FIG. 21—various steps in releasing a strap, FIGS. 22 and 23—various forms of end stops, FIGS. 24 to 26—different ways to adjust an applied force and FIGS. 27 and 28—further examples of an embodiment of the invention.

FIG. 1 shows a user 2 wearing a device for supporting an arm 4. The device features an arm support element 6, which comprises a spacer element 8 and an arm shell 10. The arm support element 6 is arranged at its distal end via a sleeve 12 on the arm 4.

The device also features a counter bearing 14, which comprises a counter bearing element 16 and a force transmission element 18. The spacer element 8 of the arm support element 6 is arranged via a joint 20 to the upper end of the force transmission element 18 depicted in FIG. 1. This is designed in the form of a rod, for example. In the example of an embodiment depicted, the force transmission element 18 is a telescopic rod. In the example of an embodiment shown, the lower end of the force transmission element 18 is arranged on the counter bearing element 16 via a ball joint 22. The counter bearing element 16 serves to transmit the forces arising to a stable element. It may lie on a ground, an object or a body part. In the example of an embodiment depicted, the counter bearing element 16 is a hip strap that lies in the 2 hip region of the user 2. The length of the counter bearing element 16 can be set by way of an adjustment device 24. On the one hand, this is convenient for the user 2 and on the other hand, it is practical for achieving as exact a positioning as possible of the ball joints 22 on the body of the user 2.

The device shown in FIG. 1 also has a passive actuator 26, which is designed in the form of a tension spring in the example of an embodiment shown. The lower end of the passive actuator 26 shown in the FIG. 1 is arranged on the force transmission element, whereas the opposite end engages with a lever element 28 of the spacer element 8 of the arm support element 6. A force is applied to the lever element 28, and thereby the spacer element 8 of the arm support element 6, by the passive actuator 26, said force counteracting the force of gravity and supporting the arm 4 of the user 2.

The device shown in FIG. 1 comprises two arm support elements 6, two counter bearings 14 and two passive actuators 26, only one of which has been described for the sake of clarity.

Figure 2:
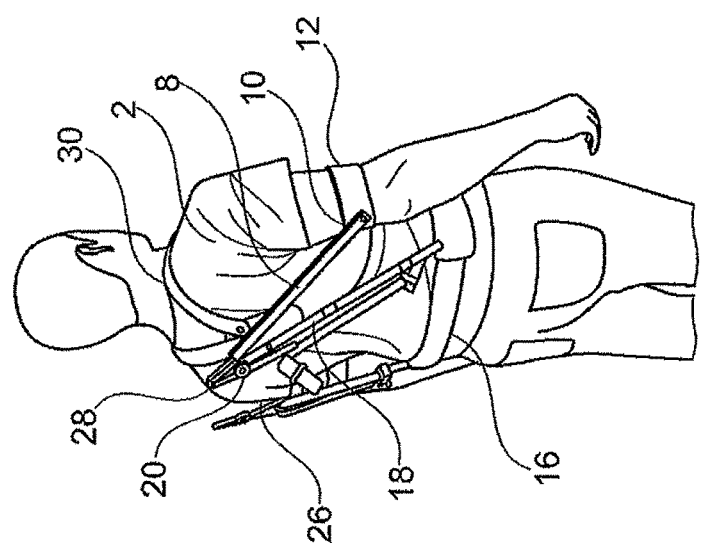

The FIGS. 2 to 6 depict a device according to an example of an embodiment of the present invention in a mounted state, wherein the user 2 has executed a range of movements. FIG. 2 shows the user 2 in a relaxed standing position, while in FIG. 3 the user 2 can be seen with spread arms. The respective arm shell 10 is attached to the arm via a sleeve 12 and, together with the spacer element 8, forms the arm support element 6. It is connected to the force transmission element 18 via the joint 20, wherein the respective force transmission elements 18 are arranged on the counter bearing element 16 in the form of a hip strap. The lever element 28, with which the passive actuator 26 engages, is situated on the joint 20.

Figure 3:
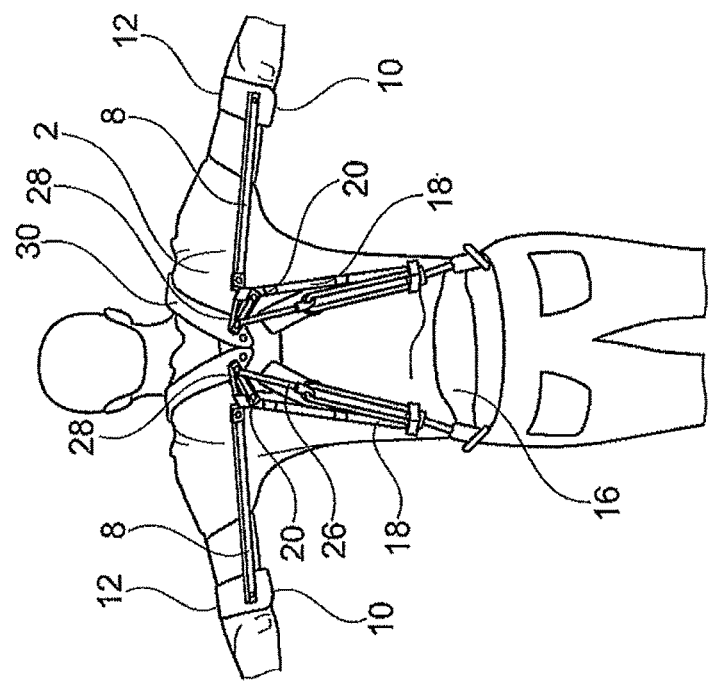

In FIG. 2, in a relaxed standing position, it is clear to see that the joint 20 moves backwards away from the user's 2 body. If the user 2 spreads his arms, as shown in FIG. 3, the respective joint 20 moves towards the body of the user 2. In the example of an embodiment depicted, the joint 20 is situated in the vicinity of the shoulder joint. The device also features two shoulder straps 30 which hold the device on the body. They do not serve to keep the joints 20 at a predetermined distance from the body.

Figure 4:
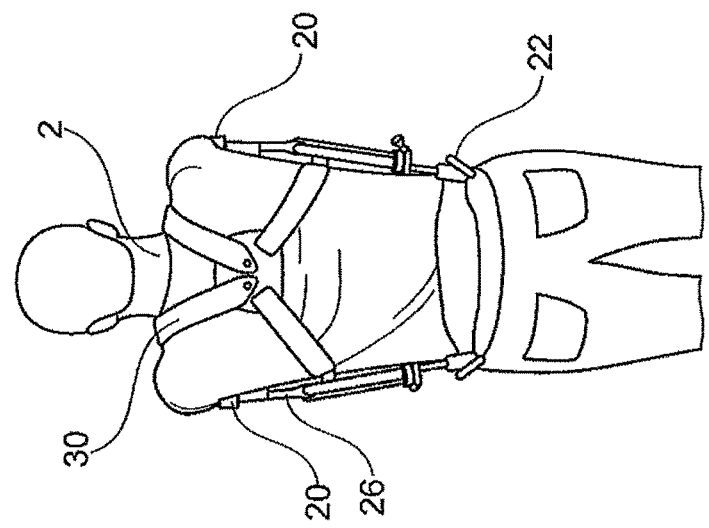

FIG. 4 shows a further raising of the arms in comparison to FIG. 3. The arms in FIGS. 4 and 5 are also moved further forwards by the user 2. It is clear that the two joints 20 move away from one another and in particular are not connected to the shoulder straps 30 in order to maintain a predetermined distance. Rather, the joints 20 and the force transmission elements 18 and the spacer elements 8, which are connected to one another via the joints 20, move outwards and can be moved almost completely freely. It is evident that the device can function without any complicated supplementary articulation mechanisms or rigid splint system. Whereas the joints 20 in FIGS. 3 and 4 are still behind the body of the user 2 in the shoulder blade region, in FIG. 5 they have moved to the sides of the body and are therefore able to follow the movement. FIG. 6 shows the position depicted in FIG. 5 in a lateral view. The arms 4 of the user 2 cross over and, as depicted in FIG. 6, the joints 20 are situated next to the shoulder of the user 2. At the same time, the ball joints 22, by means of which the force transmission element 18 is arranged on the counter bearing element 16, have not changed. The position of these ball bearings 22 remains unchanged, regardless of any movement of the arms 4 of the user 4. Such a freedom of movement achieved with such low structural complexity is barely possible with devices known from the prior art.

FIGS. 7 to 9 show a top view of various positions of the user 2 and his arms 4. In FIG. 9, the arms are widely spread out and are moved forwards via the positions in FIGS. 7 and 8 until they cross, as shown in FIG. 8. It is clearly shown how the joints 20 move outwards from FIG. 9 via FIG. 7 to FIG. 8 and stay consistently very close to the body of the user 2 in the process.

FIG. 10 shows the schematic depiction of a joint according to another example of an embodiment. The spacer elements 8 can be seen, which are connected to the force transmission elements 18 via joints 20. Unlike the examples of an embodiment depicted in FIGS. 2 to 9, there is now one connection element 32 between the two force transmission elements, said connection element being designed as an elastic strap in the example of an embodiment shown. The length of the strap can be adjusted by way of a clasp 34, such that the applicable tensile force is adjustable.

The two shoulder straps 30 are also depicted, by means of which the device 1 can be arranged on the 2 body of the user 2. The counter bearing element is not shown. This is shown in FIG. 11. It comprises another strap 36, which features a padding 38 on the side facing the body so as to render the device as comfortable as possible to wear. The force transmission element 18 is inserted into a pocket 40 provided specifically for this purpose and can be swivelled inside said pocket, thereby performing the function of a ball joint. The particularly simple structure that this entails means that complicated joint arrangements can be avoided.

Figure 12:
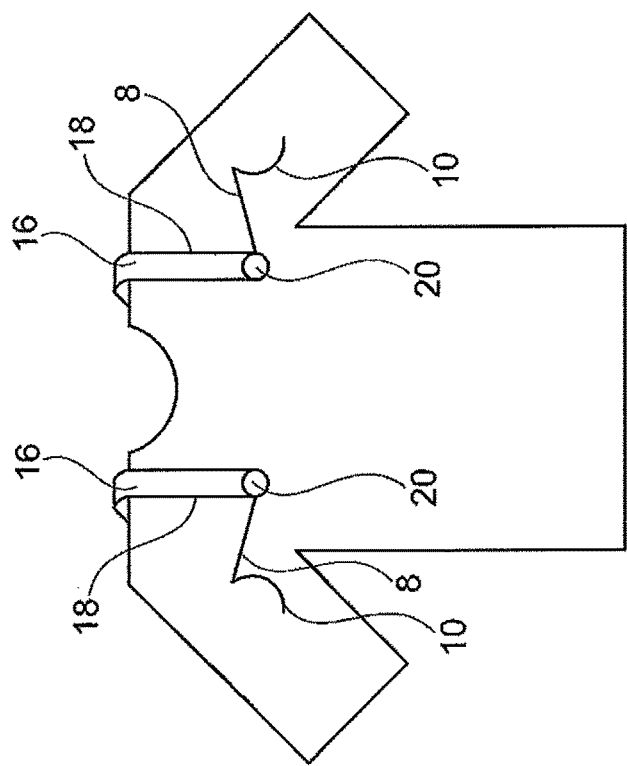

FIG. 12 shows the schematic depiction wherein the device has been integrated into an item of clothing, in this case a t-shirt. The counter bearing element 16 now consists of two shoulder elements that are connected to the spacer elements 8 and the arm shells 10 via the force transmission elements 18 and corresponding joints 20. The fact that the device is integrated into a t-shirt renders it especially easy to mount and remove, thereby eliminating the need for complicated movements. This increases the acceptance of the device.

Figure 13:
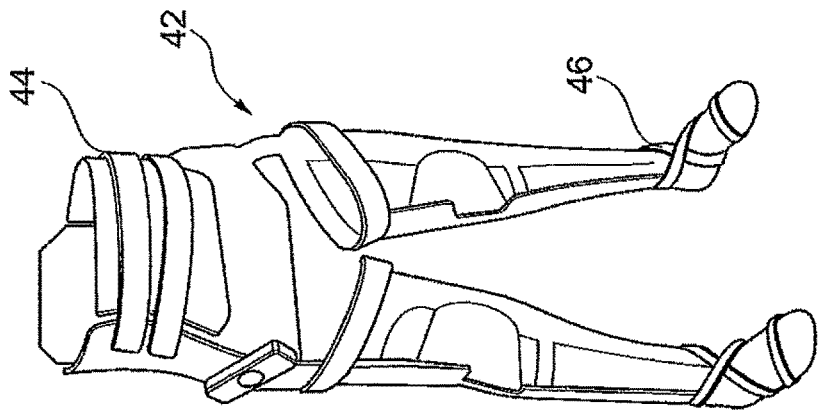

FIG. 13 depicts an exoskeleton with various splints and joints, by means of which a force from a hip element 44 can be introduced into ground contact elements 46 that are specifically provided for this purpose.

Figure 14:
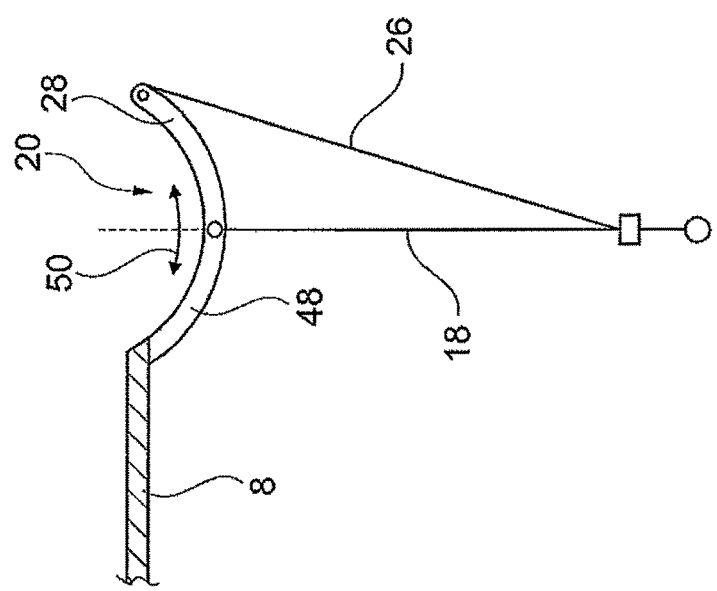

FIG. 14 shows the schematic depiction according to another configuration of the joint 20. A pivot lever 48 connects the spacer element 8 and the force transmission element 18, the upper end of which in FIG. 14 is moveably arranged in an elongated hole, not depicted, or a slot. During swivelling, the articulation point of the force transmission element 18 on the pivot lever 48 now shifts in the direction of the double arrow 50. This results in a change in the length of the lever element 28 and hence also in the force applied by the passive actuator 26.

FIG. 15 depicts a further configuration wherein, unlike with the previous configurations, the passive actuator 26 is not arranged between the lever element 28 and the force transmission element 18, but rather between the lever element 28 and the distance element 8. A preload is applied to the passive actuator 26 via a counter tensioner 52, whose position on the force transmission element 18 can be shifted along the double arrow 50.

The FIGS. 16 and 17 show various force patterns that may be applied to the arm by the device according to examples of an embodiment of the present invention. An anteversion angle is plotted on the X axis. The anteversion is the raising of the arm in a sagittal plane, i.e. forwards in the present example. 0° corresponds to the loosely hanging arm. FIG. 16 shows that a force is not applied until a predetermined angle has been reached. A torque ratio is plotted on the Y axis. The torque generated by the net weight of the arm and the force of gravity has been divided by the torque effected by the device.

The various force patterns can be adjusted on an almost individual basis and, in the example of an embodiment shown, generated by a single passive actuator 26 that is pretensioned to varying degrees. While the dotted line has been generated by a passive actuator 26 which features almost no preload, the preload increases across the dashed line and the solid line.

FIG. 17 also depicts the force that can be applied to the arm via the angle of an anteversion, yet wherein the preload of the actuator now remains unchanged. Instead, an articulation point is shifted via which the passive actuator 26 transfers its force to the support element 6. In this case, the distance of the force articulation point from the torque of the joint 20 increases from the dotted line, via the dashed line to finally reach the solid line. It is clear that, as a result, it is possible to achieve an increase in force across a broad angular range, in particular at big angles from approx. 150° upwards; however, this results in the emergence of a considerably different pattern to the patterns shown in FIG. 16.

FIG. 18 shows the device in its almost mounted state. The counter bearing element 16 in the form of a hip strap is still open, whereas the arm shells 10 have already been closed around the arm 4 of the user by way of a fastening element 54. The spacer elements 8 are arranged on the respective force transmission element 18 via a joint 20, wherein the force transmission element is arranged in a cladding 56. The passive actuator 26 is designed in the form of an elastic cable or wire. A tension element 58 is arranged on the spacer elements 8, said tension element connecting the two spacer elements 8 and thus the two arm support elements 6 to one another. The device also features shoulder straps 30 through whose connection element the tension element 58 is guided.

Elements of this configuration are shown in FIG. 19. On the two force transmission elements 18, one spacer element 8 of one arm support element 6 is arranged such that it can swivelled about one joint 20. The tension element 58 is situated between the two spacer elements 8, wherein the tension element runs through the connection element between the shoulder straps, which are not depicted.

The upper part of FIG. 20 depicts one of the shoulder straps 30, as well as an arm shell 10 with a fastening element 54 arranged on it. The fastening element 54 has a fixing element 60 in the form of a clasp which can engage with a loop 62 depicted in the lower part of FIG. 20 in order to close the arm shell 10 around an arm, which is not depicted. The shoulder strap 30 has a comparably designed loop 62. The fastening element 54 in an open state is depicted in the lower part of FIG. 20. The arm shell 10 no longer completely encloses the arm. The fixing element 60 is now inserted in the loop 62 of the shoulder strap 30 and can thus be stored securely. A grip element 64 is situated at the end of the fastening element 54, by means of which the fastening element 54 can be easily held.

FIG. 21 shows the various phases in the opening of a fastener 66 of the counter bearing element 16, which is preferably designed as a hip strap. Such a strap is also practical for other objects and is an invention in its own right, either as a stand-alone invention or as part of a device, especially an orthosis or prosthesis. The uppermost image depicts the fastener 66 in a closed state. It comprises a clasp, whose ratchet element 68 engages by way of positive-locking with a ratchet accommodation 70 specifically provided for this purpose. By pressing the two activation elements 72 together, the ratchet element 68 and the ratchet accommodation 70 can be separated, as shown in the second image from the top. A tensile force is exerted along the arrow 74. The third image from the top shows that this tensile force effects a tilting of the ratchet element 68 until it is in an almost vertical position in relation to the drawing plane, as shown in the fourth image from the top. A further separation of the two ends of the counter bearing element 16 is not possible as the ratchet element 68 does not pass through the loop 76 in this position. For this to happen, the ratchet element 68 must first of all be tilted, as shown in the second image from the bottom. It is only when it has reached this position that it passes through the loop 76 and the two elements can be separated from one another if a force is exerted along the arrow 74, as shown in the bottom-most image. This results in a safety mechanism being inserted into the fastener 66 that prevents a full release and thus a snapping or striking back of the individual ends of the counter bearing element 16 by a mere activation of the activation elements 72.

The left-hand image of FIG. 22 once again depicts the force transmission element 18, the spacer element 8 and the passive actuator 26. A mounting element 78 is also provided in the joint 20 region: In the left-hand image of FIG. 22, said mounting element is not yet lying on the elastic element, which acts as a passive actuator. This is different in the right-hand image of FIG. 22. It is clear to see that the mounting element 78 is lying on the elastic element, which acts as a passive actuator. Given that the mounting element 78 is preferably situated precisely on the rotational axis of the joint 20, the contact between the elastic element and the mounting element 78 prevents the elastic element from applying a force to the arm support element 6, which effects a torque on the arm support element 6. The elastic element is divided into two parts by the close-fitting mounting element 78, wherein each of these parts is able to exert a force but not to generate a torque, since the forces are directed radially towards the rotational axis of the joint 20. The angle between the arm support element 6 and the force transmission element 18, at which the mounting element 78 lies on the elastic element, is preferably adjustable. A further swivelling of the arm support 6 in a clockwise direction then occurs without a force being applied to the arm support element 6 by the elastic element, i.e. the passive actuator.

FIG. 23 shows the situation in the left-hand image. The end stop 80 would prevent a further swivelling of the spacer element 8 about the joint 20 relative to the force transmission element 18. If the device is to be stowed away, for example, or the projection 80 brought into the passive position, the projection 80 is disengaged from the spacer element 8 along the arrow 74, as shown in the second image from the left. As shown in the second image from the right, the spacer element 8 can now be freely swivelled in both directions along the double arrow 50 in relation to the force transmission element 18 and thus brought into the position depicted on the far right.

FIG. 24 shows a possible way of generating an adjustable force that is applied by the passive actuator 26. At a point of application 82, which is arranged eccentrically in relation to the joint 20, the passive actuator engages with the spacer element 8 of the arm support element 6. By using a suitable tool, a screwdriver in the example of an embodiment shown, the position of the point of application 82 relative to the swivel axis of the joint 20 can be adjusted via a positive-locking element and the eccentricity thus set and the force applied by the passive actuator 26 modified. An alternative or additional possibility is depicted in FIG. 25. Both diagrams in this figure shows a force transmission element 18 and a spacer element 8 that is arranged on it. In contrast to the diagram shown in FIG. 24, the diagram is rotated by 90°. They each have two passive actuators 26 which engage with the point of application 82 on the spacer element 8 that lies opposite. If the force is now to be adjusted, alternatively or additionally to the measure shown in FIG. 24, one or both of the passive actuators 26 can be removed and replaced by another. This also enables an adjustment of the force. Should the passive actuator 26 remain in place, so it can be used at a later point in time for example, its upper fixing loop can be arranged on the projection 84.

FIG. 26 shows the joint 20 with the spacer element 8 of the arm support element 6 and the force transmission element 18. It is clear that the application point 82 is designed to be moveable. To this end, the device has a motor 86, by means of which the gear wheels shown in the left-hand part of FIG. 26 can be driven, which causes the application point 82 to be moved. The motor can be used to bring the system into a state of minimal force, thereby almost fully—preferably fully—deactivating it, which is especially beneficial when mounting and removing the device or when the support is not necessary for other reasons.

FIGS. 27 and 28 correspond to the depiction in FIG. 18, the difference being that two further tension elements 58 are provided that are not arranged between the arm supports 6; rather, each tension element is arranged between one of the arm supports 6 and the counter bearing element 16. These also serve to hold the arm shells 10 on the arm. Furthermore, the elements for the two arms are independent of one another, such that any interference is prevented. In FIG. 28, the tension element 58 shown in FIG. 18 has also been removed.

REFERENCE LIST 2 user
4 arm
6 arm support element
8 spacer element
10 arm shell
12 sleeve
14 counter bearing
16 counter bearing element
17 mounting element
18 force transmission element
20 joint
22 ball joint
25 adjustment device
26 passive actuator
28 lever element
30 shoulder strap
32 connecting element
34 clasp
36 strap
38 padding
40 pocket
42 exoskeleton
44 hip element
46 ground contact element
48 pivot lever
50 double arrow
52 counter tensioner
54 fastening element
56 cladding
58 tension element
60 fixing element
62 loop
64 grip element
66 lock
68 ratchet element
70 ratchet accommodation
72 activation element
74 arrow
76 loop
78 mounting element
80 projection
82 point of application
84 projection
86 motor

The invention claimed is:

1. A device for supporting two arms of a user, comprising:
two arm support elements, wherein each of the two arm support elements has an arm shell for placing an arm of the two arms of the user on the arm shell;
at least one passive actuator which is configured to apply a force to at least one of the two arm support elements;
at least one counter bearing for the force to be applied by the at least one passive actuator which comprises
at least one counter bearing element in a form of a hip strap configured to be placed around a torso of the user, and
at least two force transmission elements each being connected to the at least one counter bearing element, wherein each of the at least two force transmission elements is connected to a respective one of the two arm support elements, wherein the at least two force transmission elements are configured to transfer a counter force from each of the two arm support elements to the at least one counter bearing element,
wherein each of the at least two force transmission elements is arranged on the at least one counter bearing element such that the respective force transmission element is movable relative to the at least one counter bearing element by swiveling or rotating about a longitudinal axis of the respective force transmission element.

2. The device according to claim 1, wherein one or more of the at least two force transmission elements is a compressive force transmission element to which at least one of the two arm support elements is arranged such that the compressive force transmission element is swivellable about a swivel axis.

3. The device according to claim 1, further comprising at least one tension element situated between the two arm support elements.

4. The device according to claim 1, further comprising one or more fastening elements for fastening the arm shell around an arm of the user.

5. The device according to claim 4, wherein the one or more fastening elements are fixable to another element different from the arm shell by at least one fixing element.

6. The device according to claim 2, further comprising an end stop for restricting movement of the at least one of the two arm support elements relative to the compressive force transmission element about the swivel axis.

7. The device according to claim 6, wherein the end stop is movable from an active position which restricts movement, to a passive position, which does not restrict movement.

8. The device according to claim 7, wherein the end stop is a projection on one of the at least two force transmission elements.

9. The device according to claim 1, wherein the at least one passive actuator is configured to apply the force depending on a position and/or orientation of the at least one of the two arm support elements relative to the at least one counter bearing element.

10. The device according to claim 1, wherein the at least one passive actuator is configured to apply the force in a way which is alterable by a preload of the at least one passive actuator.

11. The device according to claim 1, wherein the at least one counter bearing element comprises a fastener, wherein the fastener is configured such that at least two steps are required to open and close the fastener.

12. The device according to claim 11, wherein one end of the hip strap is configured to be guided through a loop to produce a positive-locking fit of two correspondingly designed positive-locking elements to close the fastener, wherein the positive-locking fit is selectively releasable such that the one end of the hip strap is guidable back through the loop to open the fastener.

13. The device according to claim 1, wherein the at least one passive actuator comprises at least one elastic element, and wherein the device further comprises at least one mounting element which, at a predetermined angle between the at least one of the two arm support elements and the at least one force transmission element, fits closely on the at least one elastic element, thereby changing the force that is applied to the at least one of the two arm support elements.

14. The device according to claim 13, wherein the predetermined angle and/or the change in the force to be applied is adjustable.

15. The device of claim 1, wherein the at least two force transmission elements are movable by rotation about at least one rotational axis.

16. The device of claim 2, wherein the compressive force transmission element is a rod or a splint.

17. The device of claim 3, wherein the at least one tension element is a spring.

18. The device of claim 4, wherein the fastening element is a strap.

19. The device of claim 5, wherein the another element is selected from the group consisting of a shoulder strap, one of the at least two force transmission elements, a cladding of one of the at least two force transmission elements, and the counter bearing element.

20. The device of claim 9, wherein the at least one passive actuator is configured to apply the force to the at least one arm support element eccentrically.

21. The device of claim 9, wherein the at least one passive actuator is configured to apply the force to the at least one arm support element depending on a swivel angle of the at least one arm support element about a swivel axis.

22. The device of claim 14, wherein the predetermined angle and/or the change in the force to be applied is adjustable by ensuring that a mounting element is shiftable relative to the at least one of the two arm support elements and/or is shiftable relative to the at least one force transmission element.

23. The device according to claim 1, wherein the at least one passive actuator is configured to apply the force in a way which is alterable by an adjustable eccentricity of the at least one arm support element.

\* \* \* \* \*